(12) United States Patent
Takahashi et al.

(10) Patent No.: US 10,830,763 B2
(45) Date of Patent: Nov. 10, 2020

(54) COMPONENT ANALYSIS DEVICE, DRUG COMPONENT ANALYSIS DEVICE, COMPONENT ANALYSIS METHOD, AND DRUG COMPONENT ANALYSIS METHOD

(71) Applicant: Hitachi High-Technologies Corporation, Tokyo (JP)

(72) Inventors: Ryosuke Takahashi, Tokyo (JP); Katsuhiro Kanda, Tokyo (JP); Yusuke Shimizu, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 74 days.

(21) Appl. No.: 15/565,959

(22) PCT Filed: Jan. 5, 2016

(86) PCT No.: PCT/JP2016/050093
§ 371 (c)(1),
(2) Date: Oct. 12, 2017

(87) PCT Pub. No.: WO2016/166995
PCT Pub. Date: Oct. 20, 2016

(65) Prior Publication Data
US 2018/0120296 A1 May 3, 2018

(30) Foreign Application Priority Data
Apr. 17, 2015 (JP) ................ 2015-084671

(51) Int. Cl.
*G01N 33/50* (2006.01)
*C12M 1/00* (2006.01)
*C12M 1/32* (2006.01)
*C12M 1/34* (2006.01)
*C12M 3/00* (2006.01)

(52) U.S. Cl.
CPC .......... *G01N 33/5014* (2013.01); *C12M 1/00* (2013.01); *C12M 21/08* (2013.01); *C12M 23/12* (2013.01); *C12M 41/32* (2013.01); *G01N 33/5067* (2013.01)

(58) Field of Classification Search
CPC ........ C12M 1/00; C12M 21/08; C12M 23/12; C12M 41/32; G01N 33/5014; G01N 33/502; G01N 33/5067
See application file for complete search history.

(56) References Cited

U.S. PATENT DOCUMENTS

| | | | | |
|---|---|---|---|---|
| 5,616,301 A | * | 4/1997 | Moser ................ | B01L 7/52 422/562 |
| 2005/0048464 A1 | * | 3/2005 | Tian ................ | C12N 5/067 435/4 |
| 2005/0079516 A1 | | 4/2005 | Maniotis et al. | |
| 2005/0142534 A1 | | 6/2005 | Maniotis et al. | |
| 2016/0298087 A1 | * | 10/2016 | Qu ................ | C12N 5/0671 |
| 2017/0037364 A1 | * | 2/2017 | Messner ............ | C12N 5/0062 |

FOREIGN PATENT DOCUMENTS

| | | |
|---|---|---|
| JP | 08-503610 A | 4/1996 |
| JP | 2007-526743 A | 9/2007 |
| JP | 2012-065659 A | 4/2012 |
| WO | 00/55355 A2 | 9/2000 |
| WO | 2015/080106 A1 | 6/2015 |

OTHER PUBLICATIONS

Defintion of "measure" downloaded from https://www.bing.com/search?q=definition+of+measure&FORM=QSRE6 on Jan. 11, 2020 (Year: 2020).*
Extended European Search Report received in corresponding European Application No. 16779787.7 dated Oct. 25, 2018.
Roggenbeckm B. A. et al., "Characterization of Arsenic Hepatobiliary Transport Using Sandwich-Cultured Human Hepatocytes", Toxicological Sciences, Mar. 9, 2015, pp. 307-320, vol. 145, No. 2.
Sharma, S. et al., "Hepatobiliary Disposition of 17-OHPC and Taurocholate in Fetal Human Hepatocytes: A Comparison with Adult Human Hepatocytes", Drug Metabolism and Disposition, Nov. 5, 2012, pp. 296-304, vol. 41, No. 2.
Kenta Yoshida, et al., "Evaluation of the Contribution of the Hepatic Efflux Transporters on the Biliary Excretion of Drugs Using Sandwich-cultured Rat Hepatocytes", Jpn Pharmacol Ther, 2009, vol. 37, suppl.1, p. S53-S58.
Brandon Swift, et al., "Sandwich-Cultured Hepatocytes: An In Vitro Model to Evaluate Hepatobiliary Transporter-Based Drug Interactions and Hepatotoxicity", Drug Metab Rev., Aug. 2010, vol. 42, No. 3, p. 446-471.
International Search Report of PCT/JP2016/050093 dated Apr. 12, 2016.
Japanese Office Action received in corresponding Japanese Application No. 2015-084671 dated Aug. 27, 2019.

* cited by examiner

*Primary Examiner* — Susan M Hanley
(74) *Attorney, Agent, or Firm* — Mattingly & Malur, PC

(57) ABSTRACT

Provided is a component analysis device, which comprises an analysis unit for measuring a component fed to the plurality of containers and analyzing the component thus measured, wherein the plurality of containers are at least a first container and a second container, wherein the first container retains a first solution containing a substance that releases adhesion between multiple cells forming the liver cell tissue, and the second container retains a buffer solution, and wherein the analysis unit measures an amount of the component discharged from the liver cell tissue in the first container into the first solution and an amount of the component discharged from the liver cell tissue in the second container into the buffer solution in the second container, and analyzes an amount of the component to be discharged via a bile duct in the liver cell tissue.

5 Claims, 22 Drawing Sheets

[FIG. 1]
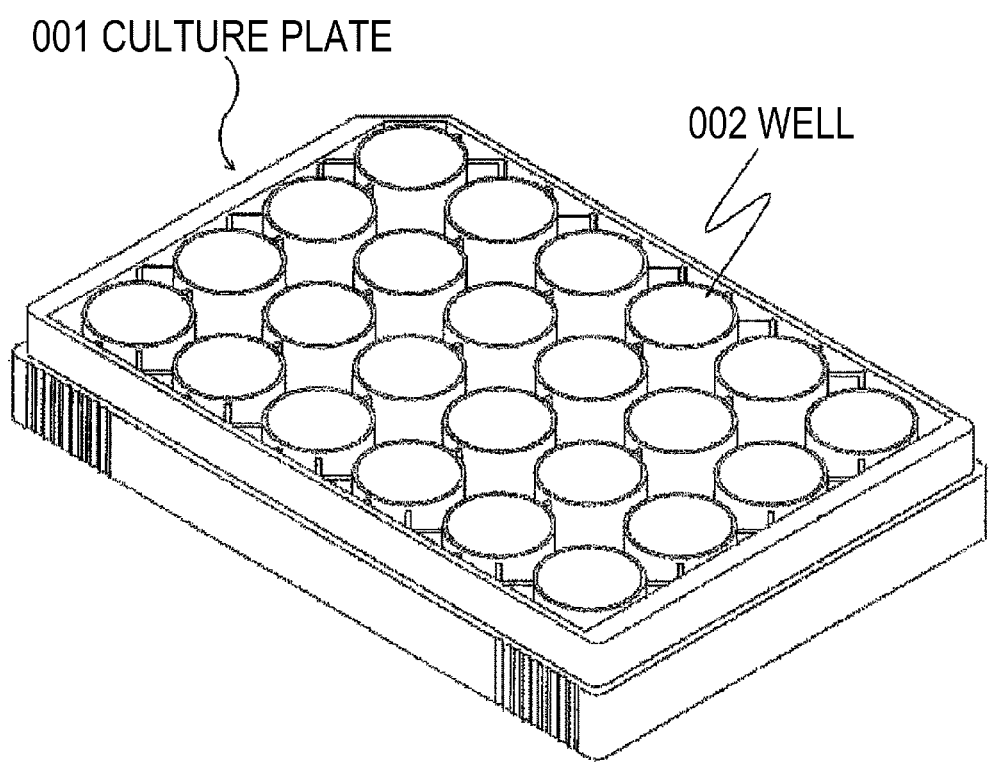

[FIG. 2]

| | STEP 0 | STEP 1 | STEP 2 | STEP 3 | STEP 4 | STEP 5 | STEP 6 |
|---|---|---|---|---|---|---|---|
| PLATE TEMPERATURE | 37°C | 37°C | 37°C→4°C | 4°C | 37°C→4°C | (DIFFERENT FOR EACH TESTING SECTION) | ROOM TEMPERATURE |
| [TESTING SECTION 1] 37°C-COLLAPSED SYSTEM | CULTURE | WASH CELLS WITH HANKS' SOLUTION TWICE, THEN PERFORM CONDITIONING WITH HANKS' SOLUTION FOR 10 MINUTES, AND THEN REMOVE HANKS' SOLUTION. | ADMINISTER DRUG SOLUTION, AND AFTER 30 MINUTES, COOL PLATE TO 4°C AND REMOVE DRUG SOLUTION. | WASH CELLS WITH ICE-COOLED HANKS' SOLUTION 3 TIMES. | | ADD HANKS' SOLUTION CONTAINING EGTA, AND AFTER 30 MINUTES, COLLECT SUPERNATANT. | (FLUORESCENCE MEASUREMENT) ADD 1% Triton X-100 SOLUTION AND COLLECT WHOLE AMOUNT OF CELL LYSATE. |
| [TESTING SECTION 2] 37°C-MAINTAINED SYSTEM | | | | | ADD HANKS' SOLUTION, AND AFTER 30 MINUTES, COOL PLATE TO 4°C AND COLLECT SUPERNATANT. | ADD HANKS' SOLUTION, AND AFTER 30 MINUTES, COLLECT SUPERNATANT. | (LCMS ANALYSIS) ADD H2O/MeOH AND COLLECT WHOLE AMOUNT OF CELL LYSATE. |
| [TESTING SECTION 3] 4°C- MAINTAINED SYSTEM | | | | | | ADD HANKS' SOLUTION, AND AFTER 30 MINUTES, COLLECT SUPERNATANT. | |

[FIG. 3]

| | STEP 4 | STEP 5 | STEP 6 | IMAGE VIEW |
|---|---|---|---|---|
| [TESTING SECTION 1] 37°C- COLLAPSED SYSTEM | BLOOD-VESSEL- SIDE DISCHARGE I DIFFUSION (1)'+ TP(2)' ⓢ1 | BILE-DUCT-SIDE DISCHARGE(3) + BLOOD-VESSEL- SIDE DISCHARGE II DIFFUSION(1) + TP(2) Ⓑ1 | INTRACELLULAR RETENTION(4) Ⓒ1 | 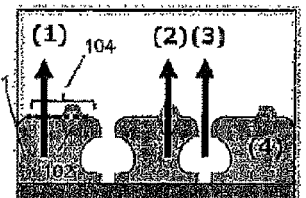 |
| [TESTING SECTION 2] 37°C- MAINTAINED SYSTEM | BLOOD-VESSEL- SIDE DISCHARGE I DIFFUSION (1)'+ TP(2)' ⓢ2 | BLOOD-VESSEL- SIDE DISCHARGE II DIFFUSION(1) + TP(2) Ⓑ2 | INTRACELLULAR RETENTION(4) + BILE-DUCT-SIDE DISCHARGE(3) Ⓒ2 | 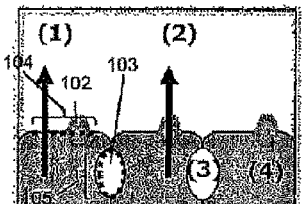 |
| [TESTING SECTION 3] 4°C- MAINTAINED SYSTEM | BLOOD-VESSEL- SIDE DISCHARGE I DIFFUSION (1)'+TP(2)' ⓢ3 | BLOOD-VESSEL- SIDE DISCHARGE II DIFFUSION(1) Ⓑ3 | INTRACELLULAR RETENTION(4) + BILE-DUCT-SIDE DISCHARGE(3) Ⓒ3 | 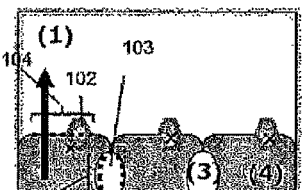 |

DIFFERENT WELLS ARE SUBJECTED TO THE SAME EXPERIMENTAL PROCEDURE (S1≅ S2≅ S3).
ACTUAL MEASUREMENTS ARE REQUIRED TO CALCULATE RELATIVE VALUES.

PATTERN 1  Ⓑ# Ⓒ#  = (1)+(2)+(3)+(4) ⇒ 100%

PATTERN 2  Ⓢ#+Ⓑ# Ⓒ# =(1)'+(2)'+(1)+(2)+(3)+(4) ⇒ 100%

[FIG. 4]

■ SAMPLE COLLECTION

| PLATE TEMPERATURE | STEP 0 | STEP 1 | STEP 2 | STEP 3 | STEP 4 | STEP 5 | STEP 6 |
|---|---|---|---|---|---|---|---|
| | 37°C | 37°C | 37°C→4°C | 4°C | 37°C→4°C | (DIFFERENT FOR EACH TESTING SECTION) | ROOM TEMPERATURE |
| [TESTING SECTION 1] 37°C-COLLAPSED SYSTEM | CULTURE | WASH CELLS WITH 400 μL OF HANKS' SOLUTION TWICE, THEN PERFORM CONDITIONING WITH HANKS' SOLUTION FOR 10 MINUTES, AND THEN REMOVE HANKS' SOLUTION. | ADMINISTER 400 μL OF 10 μM ROSUVASTATIN, AND AFTER 30 MINUTES, COOL PLATE TO 4°C AND REMOVE DRUG SOLUTION | WASH CELLS WITH 400 μL OF ICE-COOLED HANKS' SOLUTION 3 TIMES. | S1 | B1 ADD 400 μL OF TRYPSIN/EDTA, AND AFTER 30 MINUTES, PERFORM CENTRIFUGATION TO COLLECT 300 μL OF SUPERNATANT. ①②③ | C1 DISSOLVE SUPERNATANT WITH H₂O 200 μL/MeOH 800 μL AND THEN COLLECT 750 μL OF CELL LYSATE. ④ |
| [TESTING SECTION 2] 37°C-MAINTAINED SYSTEM | | | | | S2 ADD 400 μL OF HANKS' SOLUTION, AND AFTER 5-30 MINUTES, COOL PLATE TO 4°C AND COLLECT 300 μL OF SUPERNATANT. ①② | B2 ADD 400 μL OF HANKS' SOLUTION, AND AFTER 30 MINUTES, COLLECT 300 μL OF SUPERNATANT. ①② | C2 DISSOLVE SUPERNATANT WITH H₂O 200 μL/MeOH 800 μL AND THEN COLLECT 750 μL OF CELL LYSATE. ③④ |
| [TESTING SECTION 3] 4°C-MAINTAINED SYSTEM | | | | | S3 | B3 ADD 400 μL OF HANKS' SOLUTION, AND AFTER 30 MINUTES, COLLECT 300 μL OF SUPERNATANT. ① | C3 DISSOLVE SUPERNATANT WITH H₂O 160 μL/MeOH 640 μL AND THEN COLLECT 750 μL OF CELL LYSATE. ②③④ |

STEP 4.0
ADD 400 μL OF TRYPSIN/EDTA, AND AFTER 30 MINUTES, PERFORM CENTRIFUGATION, DISSOLVE PELLET WITH H₂O 160 μL/MeOH 640 μL, AND THEN COLLECT 750 μL OF CELL LYSATE. ①②③④

4-cell

① BLOOD-VESSEL-SIDE DISCHARGE FRACTION (DIFFUSION)
② BLOOD-VESSEL-SIDE DISCHARGE FRACTION (TP)
③ BILE-DUCT-SIDE DISCHARGE FRACTION
④ INTRACELLULAR RETENTION FRACTION

[FIG. 5]

|  | 2D (SANDWICH CULTURE TISSUE) | | 3D (NANOPILLAR SPHEROID) | |
| --- | --- | --- | --- | --- |
|  | $H_2O$+MeOH | Trypsin/EDTA+ $H_2O$+MeOH | $H_2O$+MeOH | Trypsin/EDTA+ $H_2O$+MeOH |
|  | TESTING SECTION 1 | TESTING SECTION 1 | TESTING SECTION 1 | TESTING SECTION 1 |
| 4-cell | 456 | 636 | 215 | 621 |
| STEP 4 | 346 | 428 | 251 | 405 |
| STEP 5 | 68.2 | 127 | 42.1 | 132 |
| STEP 6 | 6.61 | 42.8 | 2.98 | 35.3 |
| TOTAL (STEPS 4+5+6) | 421 | 598 | 296 | 572 |
| TOTAL/4-cell | 92.3% | 94.0% | 138% | 92.2% |

(UNIT: nM)

[FIG. 6A]
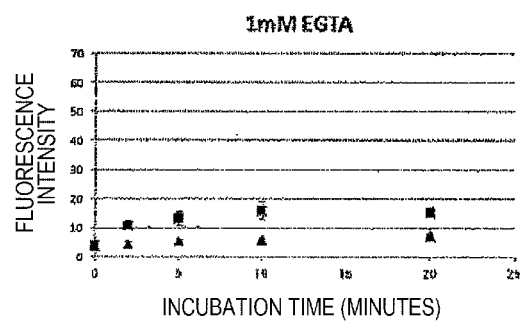
[FIG. 6B]
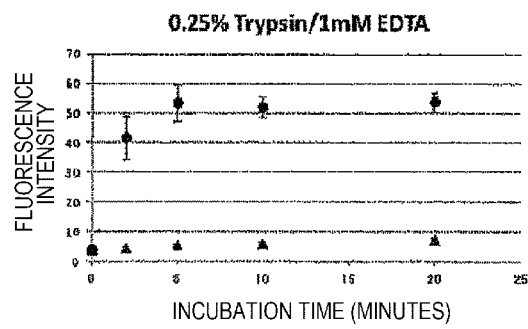

[FIG. 6C]
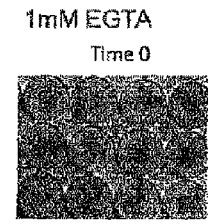
[FIG. 6D]
[FIG. 6E]
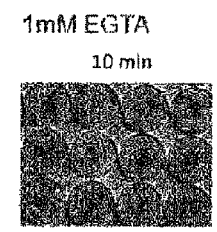
[FIG. 6F]
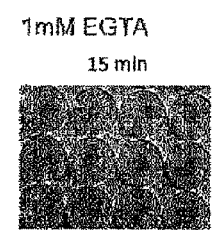
[FIG. 6G]
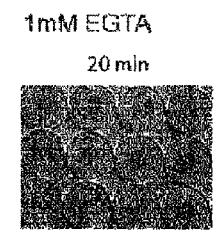

[FIG. 6H]
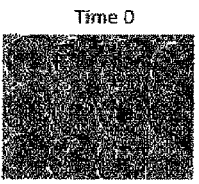
0.25% Trypsin/1mM EDTA
Time 0
[FIG. 6I]
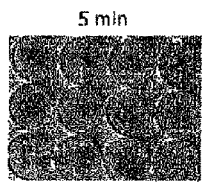
0.25% Trypsin/1mM EDTA
5 min
[FIG. 6J]
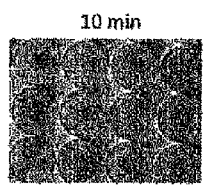
0.25% Trypsin/1mM EDTA
10 min
[FIG. 6K]
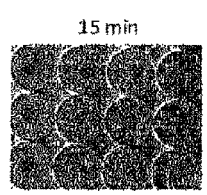
0.25% Trypsin/1mM EDTA
15 min
[FIG. 6L]
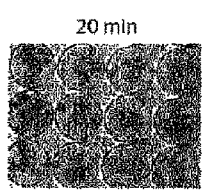
0.25% Trypsin/1mM EDTA
20 min

[FIG. 7]

| STEP | DEFINITION | PATTERN 1 | PATTERN 2 | FRACTION | CORRESPON-DENCE |
|---|---|---|---|---|---|
| 4 | FIRST BLOOD-VESSEL-SIDE DISCHARGE FRACTION (1)'+(2)' | | 70.82 | Sup | S1 |
| 5 | BILE-DUCT-SIDE DISCHARGE AND SECOND BLOOD-VESSEL-SIDE DISCHARGE FRACTION (1)+(2)+(3) | | 24.32 | | B1 |
| 5 | SECOND BLOOD-VESSEL-SIDE DISCHARGE FRACTION (1)+(2) | | 18.90 | | B2 |
| 5 | SECOND BLOOD-VESSEL-SIDE DISCHARGE FRACTION (ONLY DIFFUSION) (1) | 38.15 | 11.13 | ExEfx-Dif | B3 |
| 5 | SECOND BLOOD-VESSEL-SIDE DISCHARGE FRACTION (ONLY VIA TP) (2) | 26.60 | 7.76 | ExEfx-TP | B2 - B3 |
| 5 | BILE-DUCT-SIDE DISCHARGE FRACTION (3) | 18.58 | 5.42 | BCEfx | B1 - B2 |
| 6 | INTRACELLULAR RETENTION FRACTION (4) | 16.67 | 4.86 | Cell | C1 |
| 6 | BILE-DUCT-SIDE DISCHARGE FRACTION AND INTRACELLULAR RETENTION FRACTION (3)+(4) | 30.88 | 9.01 | | C2 |
| TOTAL | | 100.00 | 100.00 | | |

[FIG. 8A]
CIRCULAR GRAPH OF PATTERN 1: 10 µM CDF
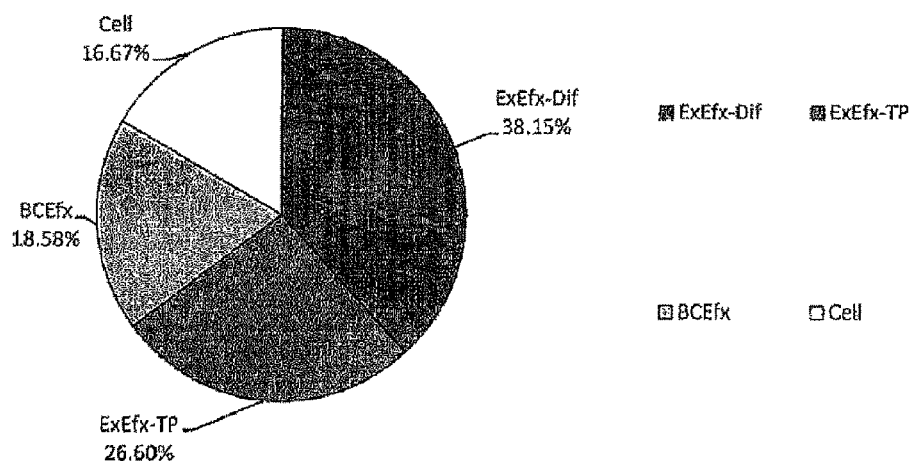
[FIG. 8B]
CIRCULAR GRAPH OF PATTERN 2: 10 µM CDF
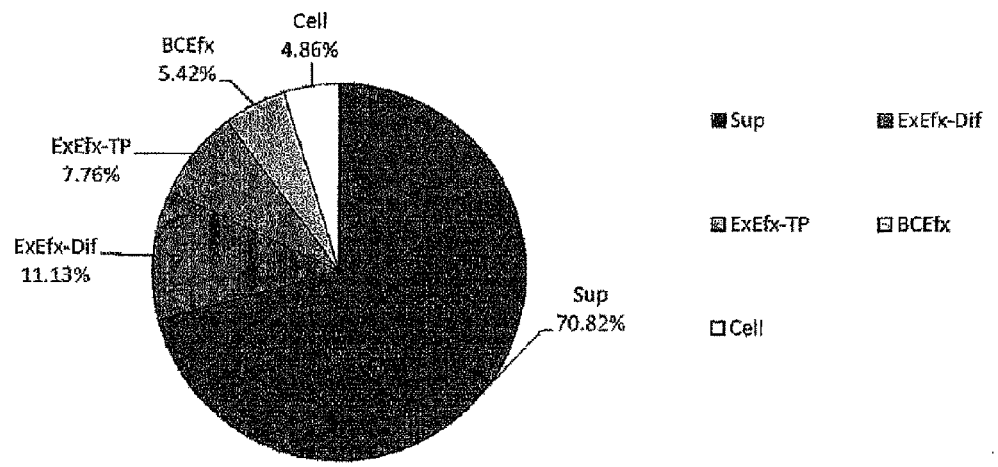

[FIG. 9A]
CIRCULAR GRAPH OF PATTERN 1: 10 μM Rhodamine 123
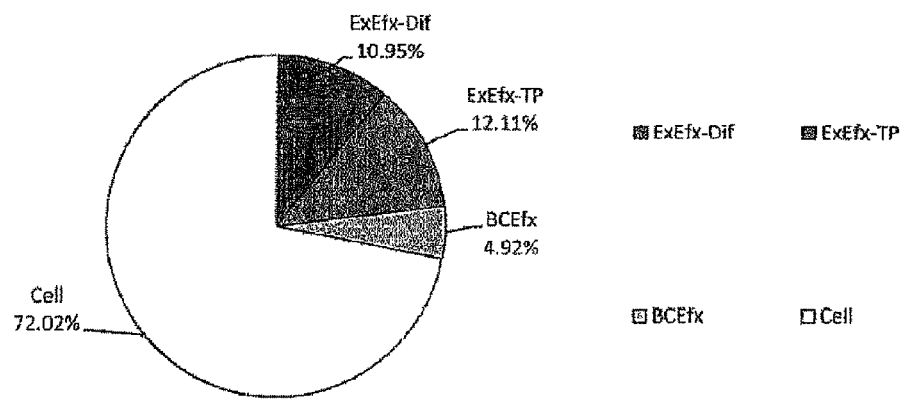
[FIG. 9B]
CIRCULAR GRAPH OF PATTERN 2: 10 μM Rhodamine 123
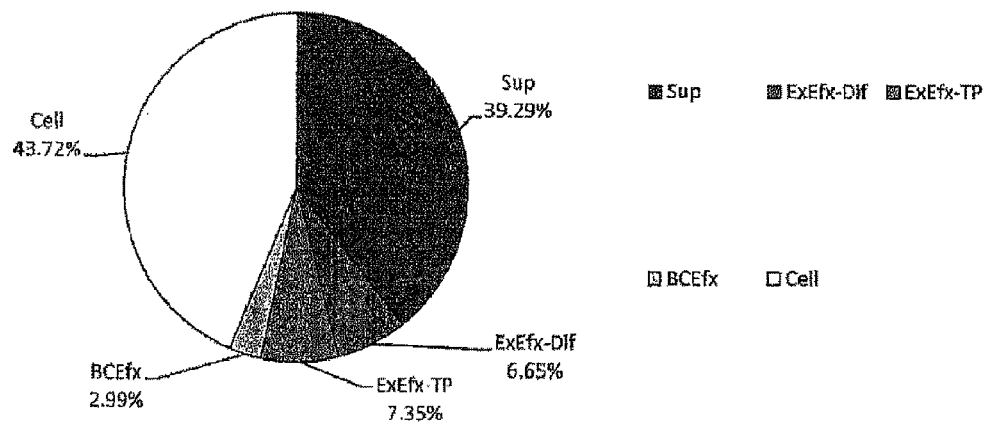

[FIG. 10]
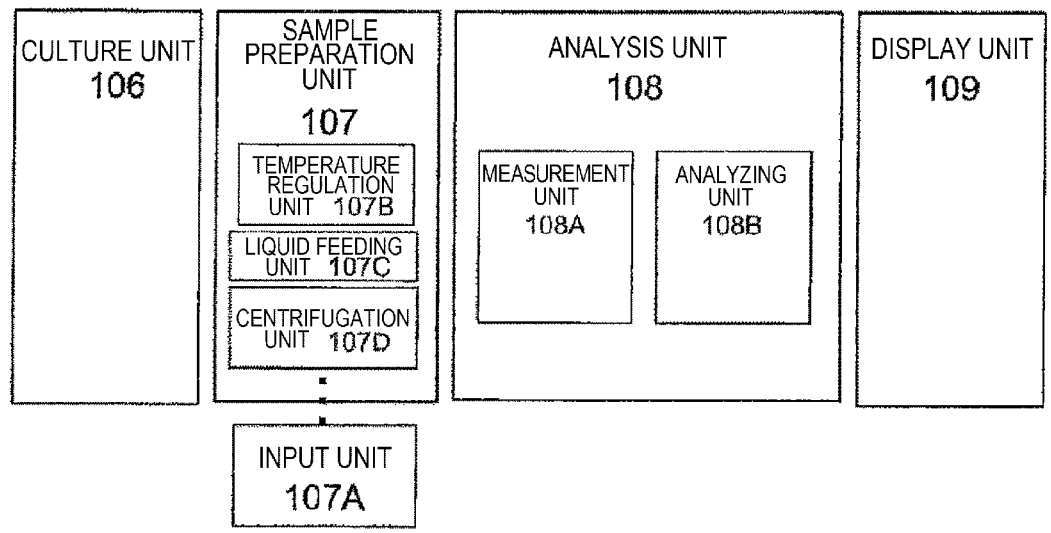

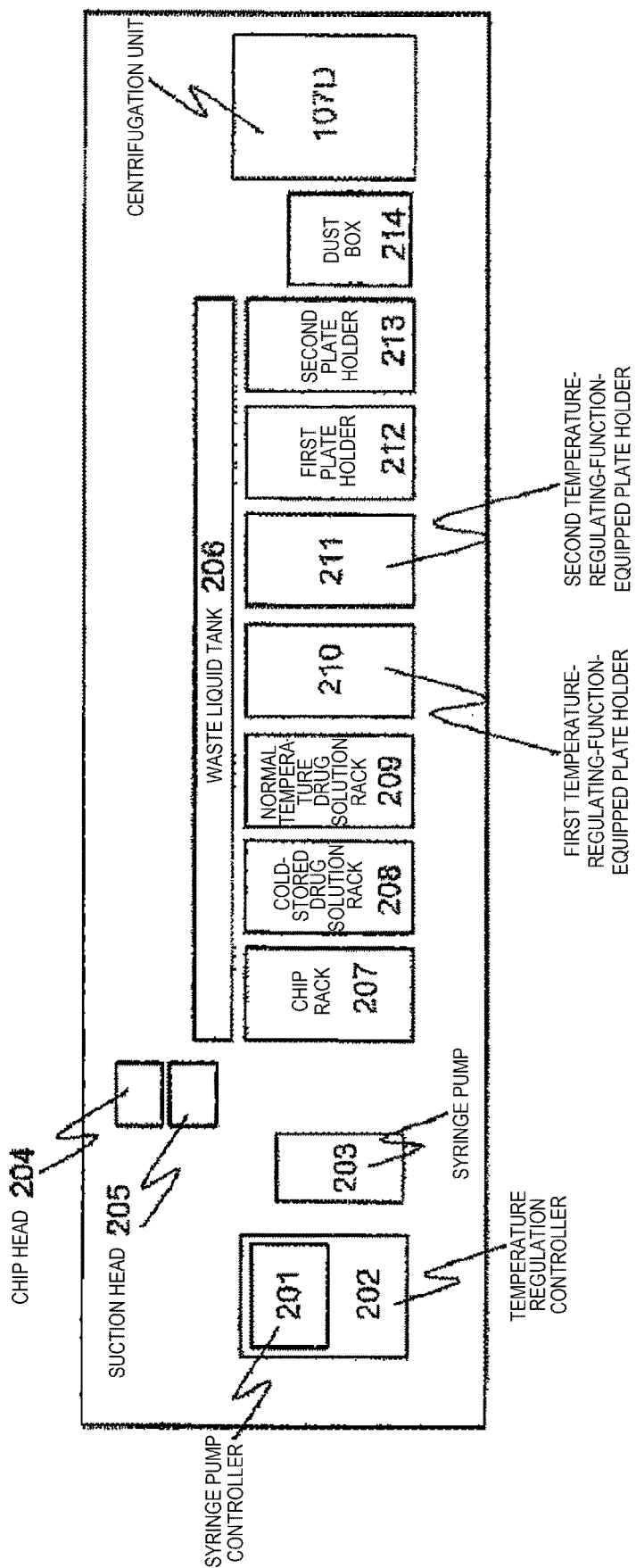

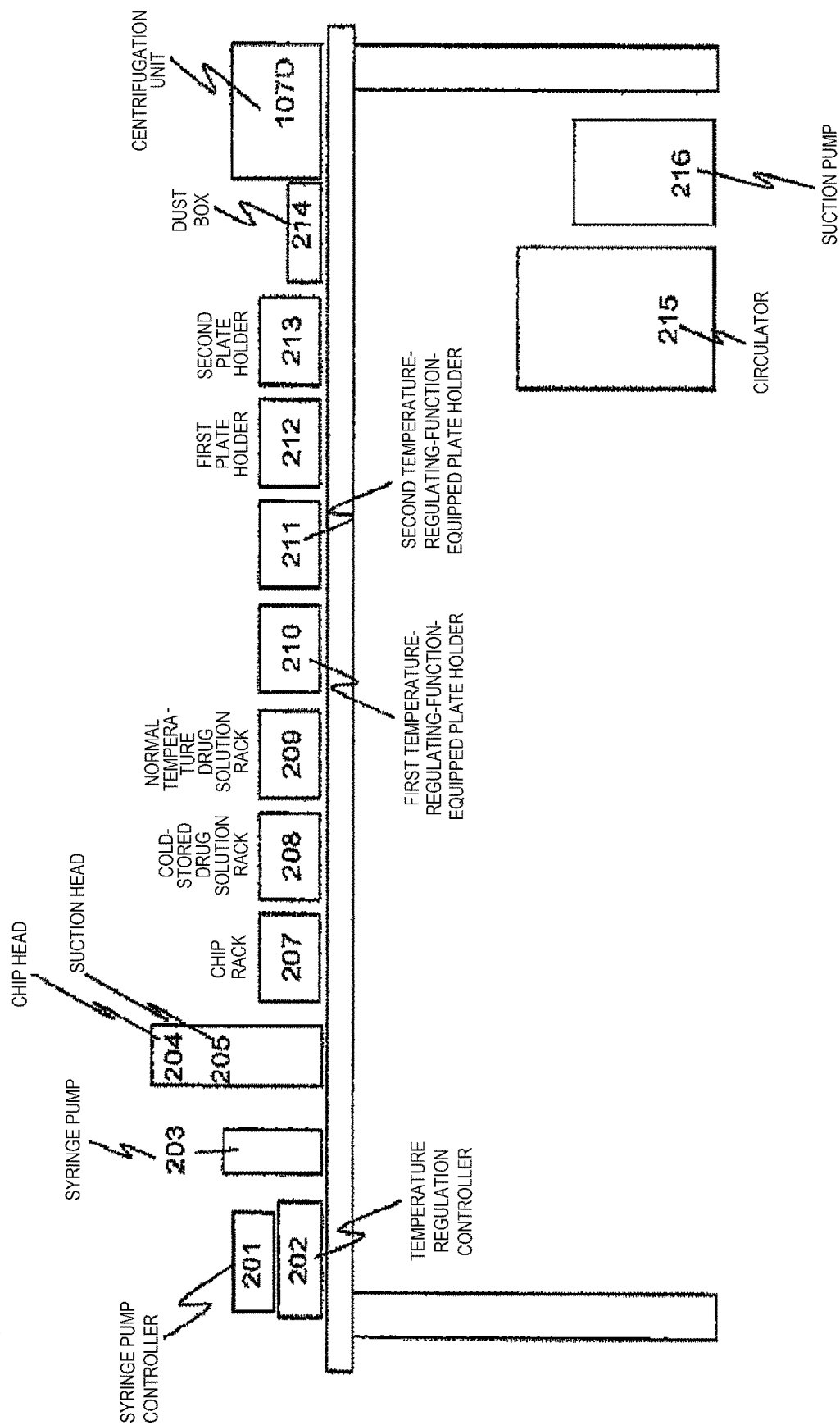
[FIG. 12]

[FIG. 13A]

| STEP NO. | SUB-STEP NO. | OPERATION | PLATE TEMPERATURE |
|---|---|---|---|
| 0 | 1 | CULTURE CELLS. | 37°C |
| - | 2 | MOVE CULTURE PLATE RETAINING CELLS FROM CULTURE UNIT TO SAMPLE PREPARATION UNIT, AND SET PLATE IN SAMPLE PREPARATION UNIT. | 37°C |
| 1 | 3 | REMOVE MEDIUM FROM CULTURE PLATE SET. | 37°C |
| 1 | 4 | SUCK BUFFER FROM DRUG SOLUTION RACK. | 37°C |
| 1 | 5 | ADD BUFFER TO EACH WELL OF CULTURE PLATE. | 37°C |
| 1 | 6 | REMOVE BUFFER FROM EACH WELL OF CULTURE PLATE. | 37°C |
| 1 | 7 | REPEAT 4-6 TWICE. | 37°C |
| 1 | 8 | SUCK BUFFER FROM DRUG SOLUTION RACK. | 37°C |
| 1 | 9 | ADD BUFFER TO CULTURE PLATE AND PERFORM CONDITIONING FOR 10 MINUTES. | 37°C |
| 1 | 10 | REMOVE BUFFER FROM EACH WELL OF CULTURE PLATE. | 37°C |
| 2 | 11 | SUCK DRUG SOLUTION FROM DRUG SOLUTION RACK. | 37°C |
| 2 | 12 | ADD DRUG SOLUTION TO CULTURE PLATE AND PERFORM INCUBATION FOR 30 MINUTES. | 37°C |
| 2 | 13 | CHANGE CULTURE PLATE HOLDER FROM 37°C TO 4°C. | 37°C→4°C |
| 2 | 14 | REMOVE DRUG SOLUTION FROM EACH WELL OF CULTURE PLATE. | 4°C |
| 3 | 15 | SUCK BUFFER REGULATED TO 4°C FROM DRUG SOLUTION RACK. | 4°C |
| 3 | 16 | ADD BUFFER TO EACH WELL OF CULTURE PLATE. | 4°C |
| 3 | 17 | REMOVE BUFFER FROM EACH WELL OF CULTURE PLATE. | 4°C |
| 3 | 18 | REPEAT 13-15 3 TIMES. | 4°C |
| - | 19 | CHANGE CULTURE PLATE HOLDER FROM 4°C TO 37°C. | 4°C→37°C |
| 4 | 20 | SUCK BUFFER FROM DRUG SOLUTION RACK. | 37°C |
| 4 | 21 | ADD BUFFER TO CULTURE PLATE, AND PERFORM INCUBATION FOR 30 MINUTES. | 37°C |
| 4 | 22 | CHANGE CULTURE PLATE HOLDER FROM 37°C TO 4°C. | 37°C→4°C |
| 4 | 23 | COLLECT SUPERNATANT FROM EACH WELL OF CULTURE PLATE TO ANOTHER MULTI-WELL PLATE. | 4°C |
| - | 24 | CHANGE CULTURE PLATE HOLDER FROM 4°C TO 37°C. | 4°C→37°C |

[FIG. 13B]

| STEP NO. | SUB-STEP NO. | OPERATION | PLATE TEMPERATURE |
|---|---|---|---|
| 5 | 25 | [WELL FOR TESTING SECTION 1] SUCK BUFFER CONTAINING EGTA FROM DRUG SOLUTION RACK. | 37°C |
| 5 | 26 | [WELL FOR TESTING SECTION 1] ADD BUFFER CONTAINING EGTA TO CULTURE PLATE AND PERFORM INCUBATION FOR 30 MINUTES. | 37°C |
| 5 | 27 | [WELL FOR TESTING SECTION 2] SUCK BUFFER FROM DRUG SOLUTION RACK. | 37°C |
| 5 | 28 | [WELL FOR TESTING SECTION 2] ADD BUFFER TO CULTURE PLATE AND PERFORM INCUBATION FOR 30 MINUTES. | 37°C |
| 5 | 29 | [WELL FOR TESTING SECTION 3] SUCK BUFFER FROM DRUG SOLUTION RACK. | 4°C |
| 5 | 30 | [WELL FOR TESTING SECTION 3] ADD BUFFER TO CULTURE PLATE AND PERFORM INCUBATION FOR 30 MINUTES. | 4°C |
| 5 | 31 | [WELL FOR TESTING SECTION 1] COLLECT SUPERNATANT FROM WELL FOR TESTING SECTION 1 INTO ANOTHER MULTI-WELL PLATE. | 37°C |
| 5 | 32 | [WELL FOR TESTING SECTION 2] COLLECT SUPERNATANT FROM WELL FOR TESTING SECTION 2 INTO ANOTHER MULTI-WELL PLATE. | 37°C |
| 5 | 33 | [WELL FOR TESTING SECTION 3] COLLECT SUPERNATANT FROM WELL FOR TESTING SECTION 1 INTO ANOTHER MULTI-WELL PLATE. | 4°C |
| - | 34 | CHANGE CULTURE PLATE HOLDER FROM 37°C/4°C TO ROOM TEMPERATURE. | 37°C/4°C→ROOM TEMPERATURE |
| 6 | 35 | SUCK 1% TritonX-100 OR PURE WATER/METHANOL FROM DRUG SOLUTION RACK. | ROOM TEMPERATURE |
| 6 | 36 | ADD 1% TritonX-100 OR PURE WATER/METHANOL. | ROOM TEMPERATURE |
| 6 | 37 | COLLECT WHOLE AMOUNT OF CELL SUSPENSION. | ROOM TEMPERATURE |
| - | 38 | MOVE PLATE CONTAINING DRUG SOLUTIONS COLLECTED TO MEASUREMENT UNIT. | - |
| - | 39 | PERFORM MEASUREMENT BY PLATE READER OR LCMS. | - |
| - | 40 | CALCULATE DISTRIBUTION RATIO INTO FRACTIONS AND SCORES FROM MEASUREMENT RESULTS. | - |
| - | 41 | DISPLAY CALCULATED VALUES ON DISPLAY UNIT. | - |

[FIG. 14]

| STEP NO. | SUB-STEP NO. | OPERATION | PLATE TEMPERATURE |
|---|---|---|---|
| 0 | 1 | CULTURE CELLS. | 37°C |
| - | 2 | MOVE CULTURE PLATE RETAINING CELLS FROM CULTURE UNIT TO SAMPLE PREPARATION UNIT, AND SET PLATE IN SAMPLE PREPARATION UNIT. | 37°C |
| 1 | 3 | REMOVE MEDIUM FROM CULTURE PLATE SET. | 37°C |
| 1 | 4 | SUCK BUFFER FROM DRUG SOLUTION RACK. | 37°C |
| 1 | 5 | ADD BUFFER TO EACH WELL OF CULTURE PLATE. | 37°C |
| 1 | 6 | REMOVE BUFFER FROM EACH WELL OF CULTURE PLATE. | 37°C |
| 1 | 7 | REPEAT 4-6 TWICE. | 37°C |
| 1 | 8 | SUCK BUFFER FROM DRUG SOLUTION RACK. | 37°C |
| 1 | 9 | ADD BUFFER TO CULTURE PLATE AND PERFORM CONDITIONING FOR 10 MINUTES. | 37°C |
| 1 | 10 | REMOVE BUFFER FROM EACH WELL OF CULTURE PLATE. | 37°C |
| 2 | 11 | SUCK DRUG SOLUTION FROM DRUG SOLUTION RACK. | 37°C |
| 2 | 12 | ADD DRUG SOLUTION TO CULTURE PLATE AND PERFORM INCUBATION FOR 30 MINUTES. | 37°C |
| 2 | 13 | CHANGE CULTURE PLATE HOLDER FROM 37°C TO 4°C. | 37°C→4°C |
| 2 | 14 | REMOVE DRUG SOLUTION FROM EACH WELL OF CULTURE PLATE. | 4°C |
| 3 | 15 | SUCK BUFFER REGULATED TO 4°C FROM DRUG SOLUTION RACK. | 4°C |
| 3 | 16 | ADD BUFFER TO EACH WELL OF CULTURE PLATE. | 4°C |
| 3 | 17 | REMOVE BUFFER FROM EACH WELL OF CULTURE PLATE. | 4°C |
| 3 | 18 | REPEAT 13-15 3 TIMES. | 4°C |
| - | 19 | CHANGE CULTURE PLATE HOLDER FROM 37°C/4°C TO ROOM TEMPERATURE. | 37°C/4°C→ROOM TEMPERATURE |
| 4 | 20 | SUCK 1% TritonX-100 OR PURE WATER/METHANOL FROM DRUG SOLUTION RACK. | ROOM TEMPERATURE |
| 4 | 21 | ADD 1% TritonX-100 OR PURE WATER/METHANOL. | ROOM TEMPERATURE |
| 4 | 22 | COLLECT WHOLE AMOUNT OF CELL SUSPENSION. | ROOM TEMPERATURE |
| - | 23 | MOVE PLATE CONTAINING DRUG SOLUTIONS COLLECTED TO MEASUREMENT UNIT. | - |
| - | 24 | PERFORM MEASUREMENT BY PLATE READER OR LCMS. | - |
| - | 25 | CALCULATE DISTRIBUTION RATIO INTO FRACTIONS AND SCORES FROM MEASUREMENT RESULTS. | - |
| - | 26 | DISPLAY CALCULATED VALUES ON DISPLAY UNIT. | - |

[FIG. 15A]

| STEP NO. | SUB-STEP NO. | OPERATION | PLATE TEMPERATURE |
|---|---|---|---|
| 0 | 1 | CULTURE CELLS. | 37°C |
| - | 2 | MOVE CULTURE PLATE RETAINING CELLS FROM CULTURE UNIT TO SAMPLE PREPARATION UNIT, AND SET PLATE IN SAMPLE PREPARATION UNIT. | 37°C |
| 1 | 3 | REMOVE MEDIUM FROM CULTURE PLATE SET. | 37°C |
| 1 | 4 | SUCK BUFFER FROM DRUG SOLUTION RACK. | 37°C |
| 1 | 5 | ADD BUFFER TO EACH WELL OF CULTURE PLATE. | 37°C |
| 1 | 6 | REMOVE BUFFER FROM EACH WELL OF CULTURE PLATE. | 37°C |
| 1 | 7 | REPEAT 4-6 TWICE. | 37°C |
| 1 | 8 | SUCK BUFFER FROM DRUG SOLUTION RACK. | 37°C |
| 1 | 9 | ADD BUFFER TO CULTURE PLATE AND PERFORM CONDITIONING FOR 10 MINUTES. | 37°C |
| 1 | 10 | REMOVE BUFFER FROM EACH WELL OF CULTURE PLATE. | 37°C |
| 2 | 11 | SUCK DRUG SOLUTION FROM DRUG SOLUTION RACK. | 37°C |
| 2 | 12 | ADD DRUG SOLUTION TO CULTURE PLATE AND PERFORM INCUBATION FOR 30 MINUTES. | 37°C |
| 2 | 13 | CHANGE CULTURE PLATE HOLDER FROM 37°C TO 4°C. | 37°C→4°C |
| 2 | 14 | REMOVE DRUG SOLUTION FROM EACH WELL OF CULTURE PLATE. | 4°C |
| 3 | 15 | SUCK BUFFER REGULATED TO 4°C FROM DRUG SOLUTION RACK. | 4°C |
| 3 | 16 | ADD BUFFER TO EACH WELL OF CULTURE PLATE. | 4°C |
| 3 | 17 | REMOVE BUFFER FROM EACH WELL OF CULTURE PLATE. | 4°C |
| 3 | 18 | REPEAT 13-15 3 TIMES. | 4°C |
| - | 19 | CHANGE CULTURE PLATE HOLDER FROM 37°C/4°C TO ROOM TEMPERATURE. | 37°C/4°C→ROOM TEMPERATURE |

[FIG. 15B]

| STEP NO. | SUB-STEP NO. | OPERATION | PLATE TEMPERATURE |
|---|---|---|---|
| 4 | 20 | SUCK TRYPSIN/EDTA FROM DRUG SOLUTION RACK. | ROOM TEMPERATURE |
| 4 | 21 | ADD TRYPSIN/EDTA AND PERFORM INCUBATION FOR 20 MINUTES. | ROOM TEMPERATURE |
| 4 | 22 | SUCK 1% TritonX-100 OR PURE WATER/METHANOL FROM DRUG SOLUTION RACK. | ROOM TEMPERATURE |
| 4 | 23 | ADD 1% TritonX-100 OR PURE WATER/METHANOL. | ROOM TEMPERATURE |
| 4 | 24 | COLLECT WHOLE AMOUNT OF CELL SUSPENSION. | ROOM TEMPERATURE |
| - | 25 | MOVE PLATE CONTAINING DRUG SOLUTION COLLECTED TO MEASUREMENT UNIT. | - |
| - | 26 | PERFORM MEASUREMENT BY PLATE READER OR LCMS. | - |
| - | 27 | CALCULATE DISTRIBUTION RATIO INTO FRACTIONS AND SCORES FROM MEASUREMENT RESULTS. | - |
| - | 28 | DISPLAY CALCULATED VALUES ON DISPLAY UNIT. | - |

[FIG. 16A]

| STEP NO. | SUB-STEP NO. | OPERATION | PLATE TEMPERATURE |
|---|---|---|---|
| 0 | 1 | CULTURE CELLS. | 37°C |
| - | 2 | MOVE CULTURE PLATE RETAINING CELLS FROM CULTURE UNIT TO SAMPLE PREPARATION UNIT, AND SET PLATE IN SAMPLE PREPARATION UNIT. | 37°C |
| 1 | 3 | REMOVE MEDIUM FROM CULTURE PLATE SET. | 37°C |
| 1 | 4 | SUCK BUFFER FROM DRUG SOLUTION RACK. | 37°C |
| 1 | 5 | ADD BUFFER TO EACH WELL OF CULTURE PLATE. | 37°C |
| 1 | 6 | REMOVE BUFFER FROM EACH WELL OF CULTURE PLATE. | 37°C |
| 1 | 7 | REPEAT 4-6 TWICE. | 37°C |
| 1 | 8 | SUCK BUFFER FROM DRUG SOLUTION RACK. | 37°C |
| 1 | 9 | ADD BUFFER TO CULTURE PLATE AND PERFORM CONDITIONING FOR 10 MINUTES. | 37°C |
| 1 | 10 | REMOVE BUFFER FROM EACH WELL OF CULTURE PLATE. | 37°C |
| 2 | 11 | SUCK DRUG SOLUTION FROM DRUG SOLUTION RACK. | 37°C |
| 2 | 12 | ADD DRUG SOLUTION TO CULTURE PLATE AND PERFORM INCUBATION FOR 30 MINUTES. | 37°C |
| 2 | 13 | CHANGE CULTURE PLATE HOLDER FROM 37°C TO 4°C. | 37°C→4°C |
| 2 | 14 | REMOVE DRUG SOLUTION FROM EACH WELL OF CULTURE PLATE. | 4°C |
| 3 | 15 | SUCK BUFFER REGULATED TO 4°C FROM DRUG SOLUTION RACK. | 4°C |
| 3 | 16 | ADD BUFFER TO EACH WELL OF CULTURE PLATE. | 4°C |
| 3 | 17 | REMOVE BUFFER FROM EACH WELL OF CULTURE PLATE. | 4°C |
| 3 | 18 | REPEAT 13-15 3 TIMES. | 4°C |
| - | 19 | CHANGE CULTURE PLATE HOLDER FROM 4°C TO 37°C. | 4°C→37°C |
| 4 | 20 | SUCK BUFFER FROM DRUG SOLUTION RACK. | 37°C |
| 4 | 21 | ADD BUFFER TO CULTURE PLATE, AND PERFORM INCUBATION FOR 30 MINUTES. | 37°C |
| 4 | 22 | CHANGE CULTURE PLATE HOLDER FROM 37°C TO 4°C. | 37°C→4°C |
| 4 | 23 | COLLECT SUPERNATANT FROM EACH WELL OF CULTURE PLATE TO ANOTHER MULTI-WELL PLATE. | 4°C |
| - | 24 | CHANGE CULTURE PLATE HOLDER FROM 4°C TO 37°C. | 4°C→37°C |

[FIG. 16B]

| STEP NO. | SUB-STEP NO. | OPERATION | PLATE TEMPERATURE |
|---|---|---|---|
| 5 | 25 | [WELL FOR TESTING SECTION 1] SUCK BUFFER CONTAINING TRYPSIN/EDTA FROM DRUG SOLUTION RACK. | 37°C |
| 5 | 26 | [WELL FOR TESTING SECTION 1] ADD BUFFER CONTAINING TRYPSIN/EDTA TO CULTURE PLATE AND PERFORM INCUBATION FOR 30 MINUTES. | 37°C |
| 5 | 27 | [WELL FOR TESTING SECTION 2] SUCK BUFFER FROM DRUG SOLUTION RACK. | 37°C |
| 5 | 28 | [WELL FOR TESTING SECTION 2] ADD BUFFER TO CULTURE PLATE AND PERFORM INCUBATION FOR 30 MINUTES. | 37°C |
| 5 | 29 | [WELL FOR TESTING SECTION 3] SUCK BUFFER FROM DRUG SOLUTION RACK. | 4°C |
| 5 | 30 | [WELL FOR TESTING SECTION 3] ADD BUFFER TO CULTURE PLATE AND PERFORM INCUBATION FOR 30 MINUTES. | 4°C |
| 5 | 31 | [WELL FOR TESTING SECTION 1] COLLECT CELL SUSPENSION FROM WELL FOR TESTING SECTION 1 INTO ANOTHER MULTI-WELL PLATE. | 37°C |
| 5 | 32 | [WELL FOR TESTING SECTION 1] CENTRIFUGE WELL AFTER COLLECTION FOR TESTING SECTION 1 TO COLLECT SUPERNATANT INTO ANOTHER MULTI-WELL PLATE. | 4°C→ROOM TEMPERATURE |
| 5 | 33 | [WELL FOR TESTING SECTION 2] COLLECT SUPERNATANT FROM WELL FOR TESTING SECTION 2 INTO ANOTHER MULTI-WELL PLATE. | 37°C |
| 5 | 34 | [WELL FOR TESTING SECTION 3] COLLECT SUPERNATANT FROM WELL FOR TESTING SECTION 1 INTO ANOTHER MULTI-WELL PLATE. | 4°C |
| - | 35 | CHANGE CULTURE PLATE HOLDER FROM 37°C/4°C TO ROOM TEMPERATURE. | 37°C/4°C→ROOM TEMPERATURE |
| 6 | 36 | SUCK 1% TritonX-100 OR PURE WATER/METHANOL FROM DRUG SOLUTION RACK. | ROOM TEMPERATURE |
| 6 | 37 | ADD 1% TritonX-100 OR PURE WATER/METHANOL. | ROOM TEMPERATURE |
| 6 | 38 | COLLECT WHOLE AMOUNT OF CELL SUSPENSION. | ROOM TEMPERATURE |
| - | 39 | MOVE PLATE CONTAINING DRUG SOLUTION COLLECTED TO MEASUREMENT UNIT. | - |
| - | 40 | PERFORM MEASUREMENT BY PLATE READER OR LCMS. | - |
| - | 41 | CALCULATE DISTRIBUTION RATIO INTO FRACTIONS AND SCORES FROM MEASUREMENT RESULTS. | - |
| - | 42 | DISPLAY CALCULATED VALUES ON DISPLAY UNIT. | - |

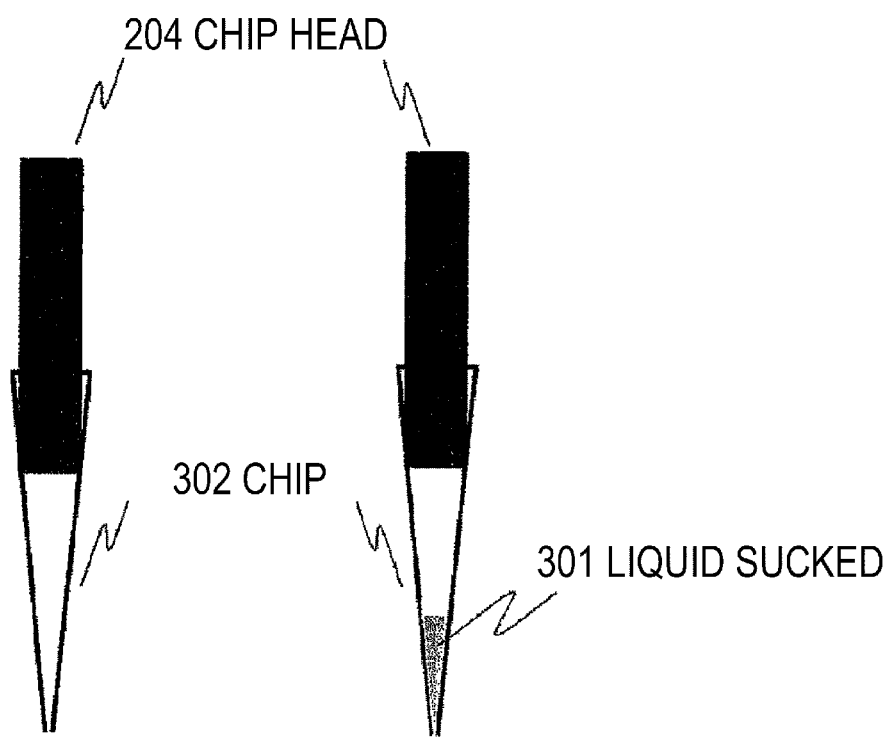
[FIG. 17]

COMPONENT ANALYSIS DEVICE, DRUG COMPONENT ANALYSIS DEVICE, COMPONENT ANALYSIS METHOD, AND DRUG COMPONENT ANALYSIS METHOD

FIELD OF INVENTION

The present invention relates to an assessment in vitro (outside the body) of an overall picture of pharmacokinetics, such as uptake, metabolism, and excretion, of a medicament, useful for new drug development.

BACKGROUND OF INVENTION

In the process of new drug development, a clinical trial ("human clinical trial") in which a drug is administered to human bodies to verify the efficacy is necessarily performed under the Pharmaceutical Affairs Act. However, a human clinical trial and an animal experiment trial require an enormous development expense. In recent years, the entire cost for new drug development has increased due mainly to such a development expense. One of main causes thereof is the fact that in the case of a drug candidate whose short medical efficacy and whose toxicity are not able to be detected in non-clinical animal experiments in an early phase of the development process, but found only in a human clinical trial in a latter phase of the development process, the previous development expenses and the expenses for the human clinical trial go to waste.

Against the background, in order to increase a pass rate of a human clinical trial to reduce the cost for new drug development, it is important to screen a new drug candidate substance that has a medical efficacy and does not show toxicity, in an early phase. Thus, many pharmaceutical companies demand an assessment system in vitro (outside the body) in which, in an early phase of a drug discovery, a drug candidate is not screened only by an animal experiment which has a small correlation with the characteristics of human cells, but pharmacokinetics of an administered medicament in human bodies can be successfully predicted using human cells.

However, a technique for grasping and dissecting an overall picture of pharmacokinetics, such as uptake, metabolism, and bile duct and blood vessel excretions, of an administered pharmaceutical candidate compound by utilizing the cells has not been established yet. In order for a drug to exhibit a medical efficacy in the body, the drug once taken into a liver is required, after being converted into a metabolism product or in a form of the original compound (parent compound) as it is without undergoing metabolism, to be discharged into a blood vessel side and then recirculate through the bloodstream again to reach a target organ or part.

Accordingly, also in a trial system in vitro, if the recirculating amount of a pharmaceutical candidate compound discharged to the blood vessel side after administration can be measured to assess the medical efficacy which is one of the most important indices in the new drug development, such a measurement can be a very useful assessment method of pharmacokinetics. In addition, by grasping an overall picture of pharmacokinetics including an amount of the compound excreted from the cells to the bile duct (elimination amount), which is then excreted out of the body with urine or feces after the bile duct excretion and an amount of the compound retained in the cells, it becomes possible to determine a distribution ratio into fractions.

PTL 1 and PTL 2 have previously disclosed a technique in which a drug is administered to cultured cells to assess an amount excreted from the bile duct of the cells (elimination amount). This assessment method assesses a drug elimination amount which is an amount of the administered drug that is excreted into the bile duct without exhibiting toxicity or a medical efficacy, and then excreted out of the body with urine or feces.

CITATION LIST

Patent Literature

PTL 1: Japanese Patent Publication No. 2012-65659
PTL 2: Japanese Patent Publication No. 8-503610

SUMMARY OF INVENTION

Technical Problem

The prior art techniques were methods which assesses a bile duct excretion amount, namely, an amount of a component that has no medical efficacy, that is, methods for assessing the out-of-body-elimination amount. However, in order to obtain information of a component having a medical efficacy, it is desired to directly assess the amount of the component excreted to the blood vessel side. In the prior art, however, a method for analyzing an amount of a compound excreted into blood vessels has not been established. Furthermore, there has not been any established assessment method in which not only a part of pharmacokinetics can be assessed, but also an overall picture of pharmacokinetics in vitro can be provided to achieve a medical efficacy assessment with a higher accuracy, by dividing an administered drug into fractions and quantifying the fractions, such as a blood-vessel (basal/basolateral)-side discharge fraction, a lumen (apical)-side discharge fraction, and an intracellular retention fraction, to determine where the administered drug is excreted from and where the drug is retained in.

Solution to Problem

For example, provided is a component analysis device, including a retention unit for retaining a plurality of containers for retaining a liver cell tissue and an analysis unit for measuring a component fed to the plurality of containers and analyzing the component thus measured, wherein the plurality of containers are at least a first container and a second container, wherein the first container retains a first solution containing a substance that releases adhesion between multiple cells forming the liver cell tissue, and the second container retains a buffer liquid, and wherein the analysis unit measures an amount of the component discharged from the liver cell tissue in the first container into the first solution and an amount of the component discharged from the liver cell tissue in the second container into the buffer liquid in the second container, to analyze an amount of the component to be discharged via a bile duct in the liver cell tissue.

Advantageous Effects of Invention

By applying the present invention, a component, such as a drug, excreted to the blood vessel side of the cells can be accessed in a direct manner. Furthermore, a blood-vessel (basal/basolateral)-side discharge fraction via a transporter and via diffusion, a lumen (apical)-side discharge fraction, and an intracellular retention fraction, of a pharmaceutical candidate compound (parent compound and metabolism product) are quantified, and the total amount of the administered pharmaceutical candidate compound and a distribution ratio into fractions are determined, whereby kinetics of the administered pharmaceutical candidate compound can be assessed, an accuracy in screening in vitro a drug candidate exhibiting a medical efficacy from among a huge number of pharmaceutical candidate compounds can be enhanced. As a result, it becomes possible to screen a pharmaceutical candidate compound in an early phase, and to reduce a wasted animal experiment and an unnecessary human clinical trial. The present invention contributes to reduction of new drug development cost which places a burden on pharmaceutical companies.

BRIEF DESCRIPTION OF DRAWINGS

FIG. 1 shows a culture plate.
FIG. 2 shows a sample preparation flow.
FIG. 3 shows objects to be quantified and medicament distribution image views for Steps 4, 5, and 6.
FIG. 4 shows a flow with 4-cell.
FIG. 5 shows a collection rates by a new protocol.
FIG. 6A shows fluorescence intensities of a collected drug in Testing section 1, Step 5.
FIG. 6B shows fluorescence intensities of a collected drug in Testing section 1, step 5.
FIG. 6C shows an effect of a dispersed drug.
FIG. 6D shows an effect of a dispersed drug.
FIG. 6E shows an effect of a dispersed drug.
FIG. 6F shows an effect of a dispersed drug.
FIG. 6G shows an effect of a dispersed drug.
FIG. 6H shows an effect of a dispersed drug.
FIG. 6I shows an effect of a dispersed drug.
FIG. 6J shows an effect of a dispersed drug.
FIG. 6K shows an effect of a dispersed drug.
FIG. 6L shows an effect of a dispersed drug.
FIG. 7 shows definitions of fractions and results for CDF.
FIG. 8A shows a distribution ratio of CDF.
FIG. 8B shows a distribution ratio of CDF.
FIG. 9A shows a distribution ratio of Rhodamine 123.
FIG. 9B shows a distribution ratio of Rhodamine 123.
FIG. 10 shows an automated measurement device configuration diagram.
FIG. 11 shows a sample preparation unit top view.
FIG. 12 shows a sample preparation unit front view.
FIG. 13A shows an automated measurement device operation flow chart.
FIG. 13B shows an automated measurement device operation flow chart.
FIG. 14 shows an automated measurement device operation flow chart.
FIG. 15A shows an automated measurement device operation flow chart.
FIG. 15B shows an automated measurement device operation flow chart.
FIG. 16A shows an automated measurement device operation flow chart.
FIG. 16B shows an automated measurement device operation flow chart.
FIG. 17 shows a chip head and a chip.

DESCRIPTION OF EMBODIMENT

Example 1

In this example, a component analysis method for the medical efficacy assessment described above will be explained along Steps 0 to 6 in FIG. 2. Steps 4 to 6 will be described in detail with reference to FIG. 3. Incidentally, in the following plural examples, although an explanation will be made based on an assessment method of a medicinal efficacious ingredient, the method is merely an example for explaining the invention of the present application, and the component analysis method of the invention of this application can obviously be applied for assessing any other chemicals than drugs, as well as medicament metabolism products. In addition, specific conditions, such as the buffer liquid, temperature, and time period, shown in this example, are merely examples, and other conditions may obviously be applied as long as they have the same effect in terms of a technical idea.

In this example, a case where at least three testing sections of Testing Sections 1 to 3 are used is explained. In each testing section, a retention area for retaining cells are present, and in the retention areas, respective containers may be used for respective testing sections, or one container having plural retention areas may be partitioned to set the respective testing sections.

<Step 0: Preparation and Culture of Liver Cells>

In this step, liver cells are prepared and cultured for verifying an effect of a drug. An example will be shown below. The preparation of liver cells was made according to an in-situ collagenase perfusion method. The detail is as follows. A rat (5 to 6 weeks old) is subjected to laparotomy under pentobarbital anesthesia, and a catheter is inserted into the portal vein and a pre-perfusion fluid (Hanks' solution not containing $Ca^{2+}$ and $Mg^{2+}$ but containing EGTA) is injected.

After thorough blood removal from the liver is confirmed, the perfusion is stopped. The perfusion fluid is replaced with a collagenase solution, and then perfusion is performed. In this example, perfusion is performed using a Hanks' solution containing 0.05% collagenase, but the perfusion fluid is not limited thereto. After digestion of the intercellular tissue by collagenase is confirmed, the perfusion is stopped. The liver is cut out, cut into elongated segments in a cooled Hanks' solution, and dispersed as cells by pipetting. Damaged liver cells are removed by centrifugation of 500 G for 5 minutes using isotonic Percoll.

The viability of the resulting liver cells is measured by the trypan blue exclusion method, liver cells of a viability of 85% or more are used for culture. Although liver cells of a viability of 85% or more are used for culture here, the present invention is obviously not limited to the condition. In addition, preparation of liver cells is not necessarily limited to the in-situ collagenase perfusion method. The liver cells to be used are not limited to those originated in a rat, and the lineage of the rat is not limited. Although liver cells were used in this example, the present invention is not limited thereto.

Liver cells prepared by the in-situ collagenase perfusion method as described above are suspended in a medium, and the liver cells in the suspension at a density of $5 \times 10^5$ cells/mL are seeded on a commercially available collagen-coated culture dish, to conduct two dimensional plane culture (for example, sandwich culture). The seeding density, medium, culture plate 001 are not particularly limited.

The culture plate is shown in FIG. 1. Although a 24-well culture plate containing 24 culture areas (wells, 002) is illustrated here, the culture plate is not limited thereto and a container having another shape may be used as long as given cells can be retained therein.

After seeding, culture is started using a $CO_2$ incubator under conditions of 5% $CO_2$ and 37° C. After 18 hours or more elapse, a first medium exchange is performed.

Although a medium used for culture from 18 hours after the seeding is not particularly limited, in this example, a medium obtained by excluding FCS from a medium (10% FCS+) to make a medium (herein after medium (FCS−)) and then adding matrigel thereto was used. After that, medium exchange is performed with the medium (FCS−) every 24 hours.

In addition, in a case where cells are cultured in a three-dimensional spheroid, that is, in this example, in a case where a three-dimensionally formed liver cell tissue is cultured, a 24-well nanopillar cell culture plate may be used. The number of wells is not particularly limited.

The cells prepared at a density of $5\times10^5$ cells/mL are seeded, and then culture is started using a CO2 incubator under conditions of 5% CO2 and 37° C. After 18 hours or more, a first medium exchange is performed. Although a medium used for culture from 18 hours after the seeding is not particularly limited, in this example, a medium obtained by excluding FCS from a medium (10% FCS+) (hereinafter, referred to as medium (FCS−)) was used.

Although a medium used for culture from 48 hours after the seeding is not particularly limited, in this example, a medium obtained by excluding FCS from a medium (10% FCS+) to make a medium (herein after medium (FCS−)) and then adding matrigel thereto was used. After that, medium exchange is performed with the medium (FCS−) every 24 hours.

As described later, since tests under different three types of conditions are conducted in Step 5 (described in detail in Testing sections 1, 2, and 3: Step 5), three culture plates having the same condition are independently prepared at this point. In Steps 0 to 4 and Step 5, the same testing operation is conducted for three types of testing sections.

<Step 1: Conditioning of Liver Cells>

In this step, cells cultured in Step 0 are conditioned to a condition suitable for a drug assessment. An example will be shown below. The culture supernatant of cells cultured for 4 days in Step 0 is removed, 400·L of a Hanks' solution is added as a buffer, and then incubation is performed at 37° C. for 10 minutes (FIG. 2, Step 1).

The kinds and amount of the buffer is not particularly limited. The operation of Step 1 is desirably repeated twice. When a component in which the cells settle is replaced from a medium used in culture in Step 0 into a buffer liquid (for example, Hanks' solution) in this manner, a groundwork can be prepared for conducting accurate measurement and dissection in the subsequent steps. However, the number of repetitions of Step 1 may obviously be arbitrarily changed depending on the kinds of the buffer liquid and the cells used.

<Step 2: Drug Solution Administration>

In this step, a drug solution to be assessed is administered to cells. An example will be shown below. After removing the buffer, 200 μL of 10 μM CDF (fluorescent reagent) is added to a well, incubation is performed at 37° C. for 30 minutes, the well is then retained at 4° C. for 5 minutes (FIG. 2, Step 2).

The kind, concentration, and amount of the reagent are not particularly limited. CDF emits fluorescence, and therefore can be easily quantified by a plate reader as a model reagent. In addition, the administered amount, which was 200 μL, was selected as such an amount that allows for all the cells in the well to be immersed in the reagent. The amount is not limited to such an amount as long as all the cells are immersed in the reagent. The CDF concentration may be any concentration that has been heretofore used in a fluorescent assay of a cell. The above concentration is desirably applied in terms of the amount of reagent for detection with a plate reader. The time period of the incubation, which was 30 minutes, was adopted based on a result of a previous study in which a time period for reaching a significant equilibrium condition in the drug intake-discharge rate was 30 minutes. The time period is not limited but depends on the purpose, and plural time periods may be combined. In addition, incubation is desirably performed using a CO2 incubator under conditions of 5% CO2 and 37° C., as with the case of Step 0.

For the purpose of preventing the administered drug from leaking outside the cells, after the incubation for 30 minutes, the plate temperature was lowered to 4° C. This is conducted for causing a phenomenon that a cell suppresses discharge of a drug to the outside when the temperature inside the container is lowered.

By lowering the temperature of the drug to a prescribed temperature or lower in this manner, the drug remains in the cells, and the phenomenon of the drug leaking out of the cells can be suppressed. The temperature, which was 4° C. in this example, is not limited thereto as long as leaking of the administered drug out of the cells can be suppressed.

In addition, the method for suppressing leaking of the administered drug out of the cells is not limited to the method of lowering the temperature if another method, for example, a method of administering an inhibitor, can be applied. In any methods, the temperature for preventing discharge or leaking of the administered drug out of cells is lower than the plate temperature upon administering the drug solution (for example, 37° C.). It is because uptake of the administered drug solution into cells is a biological phenomenon, which is considered to be typically activated at 37° C.

The timing of the drug administration is not limited to this example. For example, the drug administration is sometimes started on the day before the test day or several days earlier. In this case, the drug may be administered at Step 0 to omit Steps 1 and 2.

<Step 3: Cell Washing>

In this step, any other substances than the drug solution retained in the cells are washed off by Step 3. An example will be explained below. Next, while holding the plate at 4° C., cells are washed with 400 μL of an ice-cooled Hanks' solution 3 times (FIG. 2, Step 3).

The reason of 4° C. is the same as described above. The amount of the medium in culturing was 400 μL, and for the purpose of removing a medium component remaining on the inside wall of the well, the amount of the washing Hanks' solution was set to 400 μL. The number of times of washing in an ordinary biochemical assay, which is typically three, was followed here. The conditions of washing amount, number of times of washing, or the like are not limited. In this manner, it is possible to remove any other substances than the drug solution to be measured to enhance the accuracy of the medical efficacy assessment in the subsequent steps.

<Step 4: Blood-Vessel-Side Discharge Fraction Collection>

As one index for assessing a medical efficacy, it is effective to analyze whether an administered drug is likely to remain in cells for a long period of time or for only a short period. Thus, in this step, in order to acquire data for the index, prior to an assessment of cells in each testing section in Step 5 described later, the drug is leaked from cells for a predetermined time. An example will be shown below. First, a buffer liquid for a pretreatment (for example, Hanks' solution) was administered, incubation was performed at 37°

C. for 30 minutes, and the Hanks' solution containing the drug (supernatant) was collected (FIG. 2, step 4).

The incubation time is defined depending on the used drug and the purpose, and is not limited to 30 minutes as in this Example. In addition, the incubation is desirably performed using a CO2 incubator under conditions of 5% CO2 and 37° C., as with the case of Step 0. As for the buffer liquid, a buffer liquid of the same kind as one used in step 5 may be used, or one of other kinds may be used.

In order to discharge the drug that had been retained in the liver cell tissue (FIG. 3, 101) until Step 3 into the Hanks' solution through first blood-vessel-side discharge, that is, via passive diffusion (FIG. 2, Step 4, (1)') and via a transporter (TP) (FIG. 2, Step 4, (2)' and 102 in the image view), the temperature was maintained at 37° C. As described later, since blood-vessel-side discharge is performed also in Step 5, for discriminating them, the blood-vessel-side discharge in Step 4 was defined as the first blood-vessel-side discharge, and the blood-vessel-side discharge in Step 5 was defined as a second blood-vessel-side discharge.

Essentially, both of the steps are a step for discharge from cells to the blood vessel side (basal/basolateral) (supernatant). Alternatively, depending on the purpose, Step 4 can be considered as a washing step prior to the collection step by Step 5. A transporter is a membrane protein that is expressed on a cell membrane and has a function to transport a substance. A transporter plays a role of active substance transportation between the inside and the outside of a cell.

In addition, the passive diffusion is discharge out of the cell not through a transporter, including leaking from a cell membrane, or the like. The reason why the drug discharged into the Hanks' solution is defined as the blood-vessel-side discharge fraction in step 4 is that the top surface portion of the cell facing the Hanks' solution corresponds to a basal/basolateral surface (FIG. 3, 104), which is assumed to be a part facing a blood vessel in the body.

Step 5 explained below is a step for collecting the drug by different 3 kinds of operations (Testing sections 1, 2, and 3). By obtaining, prior to step 5, the first blood-vessel-side discharge fraction (a drug discharged into the Hanks' solution) in advance in Step 4 as described above, an index for verifying whether or not the drug is apt to remain in the cell can be acquired.

Incidentally, as the Hanks' solution used for grasping the blood-vessel-side discharge fraction, the Hanks' solution of any testing section may be used. For example, all the Hanks' solutions for Testing sections 1 to 3 may be assessed or only a part thereof may be used. In addition, Steps 3 and 4 are steps for performing the analysis of the present invention in more detail to achieve a highly accurate assessment, and these steps may obviously be skipped to perform an operation of Step 5.

Steps 0 to 4 described above are, as shown in FIG. 2, performed at least in Testing sections 1 to 3. In Step 5, in order to acquire plural index data to be determined in the present invention by analysis described later, in each of Testing sections 1 to 3, a treatment under a different condition is performed. An example of Step 5 will be shown below.

On the other hand, for quantifying the total amount of the drug administered to cells, some other cells than the cells used in Testing sections 1 to 3 are separately provided in advance, and a step for breaking the cells and collecting a cell extract solution was added between Step 3 and Step 4 (Step 4.0, FIG. 4).

A fraction obtained in this step is referred to as a 4-cell fraction. The 4-cell fraction corresponds to a container which is separately provided from the containers used in Testing sections 1 to 3, that is corresponds to a sort of Testing section 4. By adding this step, it is possible to determine the collection rate of the drug from the sum of the drug amounts collected in Testing sections 1 to 3 in the subsequent Steps 4, 5, and 6 relative to the total drug amount obtained in Testing section 4. By determining the collection rate of the drug, it is possible to assess the drug intake-discharge rate.

In the case of a fluorescence measurement, for example, either in a 2D structure such as sandwich culture or in a 3D structure such as spheroid, the drug collection and measurement of the fluorescence intensity can be performed by following the collection protocol for fluorescence measurement shown in FIG. 2, Step 6.

In addition, also in an LCMS measurement, for example, in the case of a 2D structure such as sandwich culture, the drug collection and LCMS measurement can be performed by following the collection protocol for LCMS measurement shown in FIG. 2, Step 6.

On the other hand, in the case of a 3D structure such as spheroid, collection of the whole amount of the drug has been difficult even with the collection protocol for LCMS measurement shown in FIG. 2, Step 6. Accordingly, a protocol in which trypsin/EDTA is added as described in Step 4.0 in FIG. 4 has been devised.

This aims at cutting an intercellular adhered protein by trypsin which is a proteinase to degrade spheroid into single cells, facilitating access with water and methanol, and thereby extracting the intracellular fraction efficiently.

The reagent is not limited to this reagent as long as it can release intercellular adhesion in a structure in which cells are three dimensionally arranged such as spheroid to degrade the structure into the single cells. In addition, the reagent may be any reagent that can extract the intracellular fraction in a 3D structure even not through degrading the structure into the single cells, and can be applied to a liquid chromatography mass spectrometry (LCMS) measurement. An example in which 10 M of Rosuvastatin is administered to cells and a LCMS measurement is performed to assess a drug intake-discharge rate is shown in FIG. 5.

The drug intake-discharge rate can be calculated by (Steps 4+5+6)/4-Cell×100. As a result, a collection rate in the case where a 2D structure was subjected to a water and methanol treatment was 92.3%, and a collection rate in the case where the 2D structure was subjected to a trypsin treatment, followed by a water and methanol treatment was 94.0%.

On the other hand, a collection rate in the case where a 3D spheroid was subjected to the water and methanol treatment was 138%, and a collection rate in the case where the 3D spheroid was subjected to the trypsin treatment, followed by the water and methanol treatment was 92.2%. The reason why the collection rate in the case of a 3D spheroid treated only with water and methanol exceeded 100% was considered as follows: the drug of the 4-cell fraction was not be able to be fully collected only with water and methanol and thus the sum of the drug amounts collected in the subsequent Steps 4, 5, and 6 exceeded the drug amount of the 4-cell fraction. This suggests that a trypsin treatment degrades spheroid into the single cells to facilitate access of water and methanol, and allows the intracellular fraction to be extracted efficiently.

As is apparent from the above results, in order to collect the intracellular fraction completely to obtain an precise drug intake-discharge rate, a trypsin treatment is not necessary in a 2D structure, but essential in a 3D spheroid. The reagent is obviously not limited to trypsin/EDTA as long as it is a reagent that releases intercellular adhesion to facilitate degradation into the single cells.

<Step 5, Testing Section 1: Collection of Supernatant Through 37° C.-Collapsed System>

In Testing section 1, as illustrated in Testing section 1 of FIG. 3, the total of the bile-duct-side discharge (3) and the second blood-vessel-side discharge (that is, discharge by diffusion (1) and a transporter (TP) (2)) is discharged from cells into a buffer liquid (for example, Hanks' (−) solution).

The Hanks' (−) solution is a Hanks' solution containing no calcium ion and no magnesium ion, and used in the case, such as this testing section, where intercellular adhesion is intentionally not to be strengthened. In the case of a sandwich culture with a two dimensional plane form, for the purpose of actively releasing intercellular adhesion, a chelator such as EGTA as described later is used.

Next, 200 μL of the Hanks' (−) solution containing 1 mM of EGTA was added. EGTA has a chelating function for suppressing an action of $Ca2+$ and $Mg2+$ which involve in adhesion of intercellular adhesion molecules, and is a reagent for releasing the intercellular adhesion. This allows a bile duct formed in the culture process to collapse.

After incubation at 37° C. for 30 minutes, the supernatant was collected. The incubation is desirably performed using a CO2 incubator under conditions of 5% CO2 and 37° C. as with the case of Step 0. The reagent is not limited to EGTA as long as it has a chelating function. The kind and amount of the buffer containing EGTA and the temperature and time period for the incubation are not particularly limited.

In Testing section 1 of Step 5, at the time when Step 4 is ended, all of the drug retained in the cells (FIG. 3, Step 5, and image views (1) and (2)) and the drug discharged into the bile duct (FIG. 3, Step 5 and image view (3)) are discharged into the supernatant and collected (FIG. 3, Step 5, Testing section 1).

The reason why (3) is defined as a bile-duct-side discharge fraction in Step 5 is that a cell membrane part around a gap formed in the intercellular adhesion part corresponds to an apical face (FIG. 3, 105), and that the gap is assumed as a bile canaliculi (FIG. 3, 103).

In Step 5, Testing section 1, the temperature is maintained at 37° C., and therefore a fraction discharged from cells into the blood vessel side includes a fraction via passive diffusion (FIG. 3, Step 5, (1)) and a fraction via a transporter (FIG. 3, Step 5, (2)). In addition, in the case of 3D spheroid culture, since the cells formed several layers or for other reasons, even when the treatment with a buffer containing EGTA was performed for a appropriate time period for a two dimensional sandwich culture, the intercellular adhesion release did not proceed and it was difficult to collect the bile duct discharge fraction (FIG. 6A).

For this reason, for a 3D spheroid obtained after adding 200 μL of 10 μM of CDF (fluorescent reagent) to a well in Step 2 and performing incubation at 37° C. for 30 minutes, trypsin/EDTA was used in Step 5, Testing section 1.

This was performed for the purpose as follows: since it was considered difficult for only EGTA to release the intercellular adhesion of the 3D structure composed of several layers of cells within an appropriate time period, the intercellular adhesion protein is more actively cut into the single cells with trypsin which is a protease.

The detail of the protocol is as described in FIG. 4, Testing section 1, Step 5. Results of fluorescence intensity measurements of the supernatant, taken immediately after the buffer administration, and at 2 minutes, 5 minutes, 10 minutes, and 20 minutes after administration are shown in FIG. 6B. The case of only the buffer is plotted by ▲, the case of EGTA by ■, the case of trypsin/EDTA by ●. As a result, it was found that, unlike in the case of treatment with only EGTA (■), in the case of treatment with trypsin/EDTA (●), the supernatant-side discharge amount apparently increased (FIG. 6B).

The reason was considered as follows: as is apparent from the phase contrast microscopic image in FIGS. 6C to 6L, intercellular adhesion was collapsed by the trypsin/EDTA treatment, and the bile duct discharge fraction was discharged to the supernatant side. This suggests that for completely collecting the bile duct discharge fraction from a 3D spheroid, a treatment for degrading the cells into the single cells is essential. The reagent is obviously not limited to trypsin/EDTA as long as it releases intercellular adhesion to facilitate the degradation into single cells.

<Step 5, Testing Section 2: Collection of Supernatant Through 37° C.-Maintained System>

In Testing section 2, the bile duct is not collapsed unlike in Testing section 1 and only a fraction that is called the second blood-vessel-side discharge in FIG. 3 (diffusion (1) and transporter (2)) is discharged. The Hanks' solution was added in an amount of 200 μL. Since Testing section 2 does not contain a chelating agent such as EGTA unlike Testing section 1, intercellular adhesion remains to be maintained, and therefore, in this testing section, collapse of a bile canaliculi is not induced.

After incubation at 37° C. for 30 minutes, the supernatant was collected. The incubation is desirably performed using a CO2 incubator under conditions of 5% CO2 and 37° C. as with the case of Step 0.

In Testing section 2 of Step 5, the drug retained in the cells at the time when Step 4 ends (FIG. 3, Step 5, and image view (1), (2)) is discharged into the supernatant and collected (FIG. 3, Step 5, Testing section 2). Various conditions are not limited.

According to the foregoing explanations, the drug discharged in the supernatant is defined as the second blood-vessel-side discharge fraction. In Step 5, Testing section 2, since the temperature is maintained at 37° C., a fraction discharged from cells into the blood vessel side includes a fraction via passive diffusion (FIG. 3, Step 5, (1)), and a fraction via a transporter (FIG. 3, Step 5, (2)).

By quantitatively analyzing amounts of the drug collected from Testing section 1 and Testing section 2 of Step 5, for example, by subtracting a quantified value of the amount of the drug collected in Testing section 2 from a quantified value of the amount of the drug collected in Testing section 1, a drug amount of the bile-duct-side discharge (3) can be calculated.

<Step 5, Testing Section 3: Collection of Supernatant Through 4° C.-Maintained System>

By making Testing section 3 in a lower temperature condition than Testing sections 1 and 2 as described later, as for the second blood-vessel-side discharge, the discharge of the drug from a transporter (1) is suppressed, and only the discharge fraction through diffusion (2) is discharged. After 200 μL of a Hanks' solution was added and incubation was performed at 4° C. for 30 minutes, the supernatant was collected. This testing section is different in the test temperature from Step 5, Testing section 2 that shares a common point of a maintained system.

This is because the blood-vessel-side discharge via a transporter is suppressed by adopting 4° C. In Step 5, Testing section 3, by adopting Testing section of a low temperature, 4° C. in which a transporter activity is suppressed, it is possible to quantify only a discharge amount via passive diffusion (FIG. 3, Step 5, (1)) to calculate (quantify) the blood-vessel-side drug discharge amount via a transporter in comparison with Step 5, Testing section 2.

For each drug, a specific transporter is present for moving inside and outside the cells. Accordingly, the possibility of excluding the discharge amount via passive diffusion and quantifying discharge amount via a transporter means possibility of quantifying a specific discharge amount for each drug. The kind and amount of the buffer, and the temperature and time period of incubation are not particularly limited.

By quantifying the drug collected from Testing section 2 and Testing section 3 of Step 5 in the same manner as described above, the discharge fraction via a transporter can be calculated. Incidentally, an example in which Testing sections 1, 2, and 3 are used to calculate the respective discharge fractions was described in this example, but the number of the testing sections is not necessarily limited to three.

For example, if only the bile-duct-side discharge (3) and the second blood-vessel-side discharge ((1)+(2)) are desired to be separated, only Testing sections 1 and 2 have to be conducted, and if merely the diffusion (1) and the transporter (2) are desired to be separated in the second blood-vessel-side discharge, only Testing sections 2 and 3 have to be conducted.

In addition, by separately providing a 4° C.-collapsed system as needed, as for the discharge into the bile-canaliculi-side, discharge via a transporter is suppressed, and only the discharge by diffusion can be measured. This makes it possible to separately assess the discharge into the bile canaliculi side by diffusion and the discharge into the bile canaliculi side via a transporter, for example, by comparing the 4° C.-collapsed system with Testing section 3. The steps in each of Testing sections 1 to 3 described above may be conducted in any order, or the steps may be conducted in parallel.

<Step 6: Collection of Bile Duct Fraction and Intracellular Fraction>

In Step 6, all the three testing sections return into a common operation again. In Step 6, drug collection is performed for quantifying the intracellular retention fraction. In the case where a fluorescence drug or the like is quantified with a plate reader or the like, it is desired that a Hanks' solution containing 1% of a surfactant is added, for example, in an amount of 200 µL, to suspend the cells therein, and the whole amount is collected (FIG. 2, Step 6).

This makes it possible to break a cell membrane to discharge the drug remaining in the cells. The resulting sample was transferred into a culture plate, and a fluorescence measurement was performed using a plate reader. For a blank measurement, a well in which only a Hanks' solution is added is provided. The fluorescence intensity is measured using an excitation wavelength of 484 nm and an absorption wavelength of 519 nm.

In addition, when a drug is quantified using a mass spectrometry (LCMS) device, or the like, the drug remaining in cells is extracted through making a hypotonic solution by adding water, a treatment with an organic solvent, or other procedure, and then, the cells are suspended in an organic solvent such as methanol to collect the whole amount (FIG. 2, Step 6).

Subsequently, the drug is quantified using a LCMS device as described later. Either in the case of a plate reader measurement of a fluorescence drug as described above, or in the case of a LCMS measurement of a drug, when a 3D spheroid is used as a material, a cell pellet collected after centrifugation in Testing section 1, Step 5 is subjected to the breaking step described above and the drug is quantified.

<Determination of Distribution Ratio into Fractions and Scoring Based on Measurement Results>

Based on fluorescence intensities reflecting the drug amounts obtained in the above steps, a distribution ratio into fractions is calculated. Here, the total sum of Steps 5 and 6 (FIG. 3, B #+C #=(1)+(2)+(3)+(4)) is taken as a 100% drug amount.

This case is referred to as "Pattern 1". From 6 kinds of values determined by the fluorescence amount measurements (B1, B2, B3, C1, C2, and C3), a distribution ratio into fractions as shown in FIG. 7, Pattern 1 is obtained. From the values, the second-blood-vessel-side discharge fraction only by diffusion (extracellular efflux by diffusion, ExEfx-Dif) is associated to B3, the second-blood-vessel-side discharge fraction only via a transporter (extracellular efflux by transporter, ExEfx-TP) is associated to B2-B3, the bile-duct-side discharge fraction (bile canaliculi efflux, BCEfx) is associated to B1-B2, the intracellular retention fraction (Cell) is associated to C1.

Based on the results, a circular graph, such as the graph of Pattern 1 in FIG. 8A, can be drawn, making it possible to visually understand an overall picture of the distribution ratio into fractions. Furthermore, based on the quantification results, it is possible to make a scoring peculiar for each drug as described below.

In this example, an example of a CDF score calculated will be shown. The score calculated is not limited thereto. A score for assessing a blood-vessel-side discharge via a transporter is obtained by (B2−B3)/B2 as a ratio of a drug amount discharged via a transporter relative to the second blood-vessel-side discharge drug amount (ratio of extracellular efflux by diffusion, RexEMTP). A score for assessing excretion into a bile duct is obtained by (B1−B2)/(C1+C2) as a ratio of a bile duct excretion drug amount relative to the whole drug amount taken in cells (biliary retention drug, BiRD), or, alternatively, obtained by (C2−C1)/C2, (B1−B2)/C1, or the like, as a ratio of a bile duct excretion drug amount relative to a drug amount remaining in cells.

<Comparison of Distribution Ratios and Scores Between Different Drugs>

By replacing CDF with Rhodamine 123, results shown in FIG. 9A (Pattern 1) can be obtained in the same operation as described above. It can be seen that a clearly different distribution ratio can be detected from FIG. 8A (Pattern 1) which shows results for CDF.

In addition, for example, it can be seen that the ratio of the drug amount discharged via a transporter relative to the blood-vessel-side discharge drug amount of CDF (RexEMTP) and the ratio of the bile duct excretion drug amount relative to the whole drug amount taken in the cells (BiRD) are 41.08 and 18.58, respectively, whereas those of Rhodamine 123 are 52.52 and 4.92, respectively. Thus, it can be seen that CDF is a drug that has a property of being more likely to be excreted into a bile duct and less likely to be discharged to the blood vessel side, as compared with Rhodamine 123. As described above, according to the present invention, it is possible to assess what pharmacokinetics each compound exhibits.

Example 2

In Example 2, determination of a distribution ratio into fractions and scoring based on measurement results will be explained in the case of using a different method from that in Example 1. In this example, it is possible to give, in addition to the distribution ratio into fractions shown in Pattern 1 of Example 1, information on whether or not the administered medicament is likely to remain in cells by utilizing the quantified values S # (corresponding to Step 4) shown in FIG. 3, and to achieve a more accurate assessment.

Specifically, the total sum of Step 4, 5, and 6 (FIG. 3, S #+B #+C #=(1)'+(2)'+(1)+(2)+(3)+(4)) is taken as a 100% amount of the administered medicament. This case is referred to as "Pattern 2". Accordingly, the 9 kinds (S1, S2, S3, B1, B2, B3, C1, C2, and C3) determined by the testing sections of Step 4, 5, and 6 can be used as indices for assessment.

From the 9 kinds of values determined by the fluorescence amount measurements, the distribution ratio into the fractions as shown in Pattern 2 of FIG. 7 can be obtained. From the values, the first blood-vessel-side discharge fraction (Sup fraction) is associated to S1 (≅S2≅S3), the second blood-vessel-side discharge fraction only by diffusion (extracellular efflux by diffusion, ExEfx-Dif) is associated to B3, the second blood-vessel-side discharge fraction only via a transporter (extracellular efflux by transporter, ExEfx-TP) is associated to B2–B3, the bile-duct-side discharge fraction (bile canaliculi efflux, BCEfx) is associated to B1–B2, and the intracellular retention fraction (Cell) is associated to C1.

Based on the above results, a circular graph as shown in Pattern 2 of FIG. 8B can be drawn, making it possible to visually understand an overall picture of the distribution ratio into fractions. With the methods shown in Example 2, the sup fraction which is an index for whether or not the medicament is likely to remain in the cells is 70.82 for CDF, but 39.29 for Rhodamine 123 (FIG. 9B, Pattern 2), and it can be seen that CDF tends to be discharged to the blood vessel side.

This matches the assessment of the intracellular retention fraction in Example 1. Furthermore, based on the quantification results, a scoring peculiar for the drug can be made, which is as shown in Example 1.

Example 3

In Example 3, an example of a device for realizing automation of a series of steps described in Example 1 and 2 will be described. Incidentally, descriptions of the purpose of the operation of the device described below, the role of the component thereof, and the like may be sometimes omitted when they are the same as in Example 1 or 2.

In the device configuration described below, the areas for retaining cells set for the respective Testing sections 1 to 3 shown in Examples 1 to 2 are explained with expressions of a "well for Testing section 1", "well for Testing section 2", "well for Testing section 3", and the like. As for the areas, for example, a plurality of containers each of which is the aforementioned "well culture plate" are set for the respective testing sections, or a plurality of wells in one well culture plate may be partitioned to set the partitioned areas as, for example, "a first container", "a second container", "a third container", and the like. Incidentally, in this case, the 4-cell fraction (Testing section 4) explained in Example 1 described above is another "fourth container" that is different from the first to third containers.

In particular, since the well for Testing section 1 and the well for Testing section 2 are adjusted to almost the same temperature, a more efficient assessment can be achieved in terms of the accuracy and speed when the sections are set by partitioning one well culture plate.

Incidentally, in the operation of the device described later, as for an operation for replacing a well (container) for each testing section, the well may be replaced automatically or by hand. The replacement and install operations of the containers are omitted in the following explanation.

As shown in FIG. 10, this device is composed of a culturing unit 106, a sample preparation unit 107 (including an input unit 107A), an analysis unit 108, and a display unit 109. Furthermore, the sample preparation unit 107 includes a temperature regulation unit 107B for regulating temperatures inside containers (plate(s)) described later, a liquid feeding unit 107C capable of feeding or collecting a liquid to or from the containers, and the like. The sample preparation unit is desirably under an environment of 5% $CO_2$ and 37° C.

The analysis unit 108 includes a measurement unit 108A for measuring amounts of a component such as a drug and an analyzing unit 108B for analyzing the amounts of fractions discharged via a transporter and via a bile duct, remaining in cells, and discharged from other paths than the transporter and the bile duct (diffusion) from the amounts of the component such as a drug obtained by the measurement unit. The device configuration is an example, and, for example, a configuration in which the analyzing unit is implemented by another device, to which information obtained by the measurement unit is sent, may be obviously employed.

In addition, the detailed configuration of the sample preparation unit is illustrated in FIGS. 11 and 12. As described above in Examples 1 and 2, the sample preparation unit has a role of automatically preparing the fractions to be analyzed.

Each component will be explained with reference to flowcharts described later. An automated measurement device operation flow chart is shown in FIG. 13. The flowchart of FIG. 13 is merely an example, and as described in Example 1, <step 2>, in the case where the drug is administered at a different time, the flowchart is not limited thereto. In this example, a plate including multiple cell retention areas (wells) is used as an example of a container for retaining cells, but the container is obviously not limited to a plate as long as it can retain cells.

<Transfer from Culturing Unit to Sample Preparation Unit>

First, a liver cell tissue is cultured in the culturing unit 106 (FIG. 10, FIG. 13A, Sub-step 1). Then, the plate retaining the cultured liver cell tissue is transferred onto a first temperature-regulating-function-equipped plate holder 210 and a second temperature-regulating-function-equipped plate holder (211) of a sample preparation unit (FIG. 10, FIG. 13A, Sub-step 2).

<Sample Preparation: Corresponding to Step 1 of Examples 1 and 2>

A suction head 205 which is placed in the liquid feeding unit 107C and provided with a suction nozzle for sucking a liquid is moved to a well 002 on a culture plate 001 filled with a medium to be removed, on the plate holder, and sucks the medium from the well to remove the whole amount (FIG. 13A, Sub-step 3). The medium removed is collected for disposal in a waste liquid tank 206.

Next, a chip 302 for retaining a liquid 301 is attached to a chip head 204 mounted on the suction nozzle from a chip rack 207 storing a plurality of chips. The chip head moves to a normal temperature drug solution rack 209, and sucks a buffer (FIG. 13A, Sub-step 4). The chip head moves to a target well, adds the buffer (FIG. 13A, Sub-step 5), and then moves to a dust box 214 to discard the chip. Although replaceable chips are used here for preventing contamination, the present invention is not limited thereto.

The suction head moves to the well filled with the buffer and removes the buffer (FIG. 13A, Sub-step 6). The removed medium is collected for disposal into the waste liquid tank 206. This step is repeated twice in total (washing step) (FIG. 13A, Sub-step 7).

Next, a chip in the chip rack 207 is attached to the chip head 204, and the chip head moves to the normal temperature drug solution rack 209 and sucks the buffer (FIG. 13A, Sub-step 8). The chip head moves to the target well, adds the buffer, and then moves to the dust box 214 to discard the chip. The device waits at 37° C. for 10 minutes (conditioning) (FIG. 13A, Sub-step 9). Then, the suction head 205 moves to the well filled with the buffer, and removes the whole amount of the buffer (FIG. 13A, Sub-step 10).

<Sample Preparation: Corresponding to Step 2 in Examples 1 and 2>

A chip in the chip rack 207 is attached to the chip head 204, and the chip head moves to the normal temperature drug solution rack 209, and sucks a drug solution (FIG. 13A, Sub-step 11). The chip head 204 moves to the target well, adds the drug solution (FIG. 13A, Sub-step 12), and then moves to the dust box 214 to discard the chip. The device waits at 37° C. for 30 minutes (FIG. 13A, Sub-step 12).

Then, the first temperature-regulating-function-equipped plate holder 210 and the second temperature-regulating-function-equipped plate holder 211, which constitute one configuration example of the container retention unit for retaining containers, change from 37° C. to 4° C. (FIG. 13A, Sub-step 13), then the suction head 205 moves to the well filled with the drug solution, and removes the whole amount of the drug solution (FIG. 13A, Sub-step 14). Incidentally, as the temperature regulation unit in this example, a plate holder is equipped with a temperature regulating function in this explanation, but the temperature regulation unit may obviously be present separately from the container retention unit.

<Sample Preparation: Corresponding to Step 3 in Examples 1 and 2>

A chip in the chip rack 207 is attached to the chip head 204, and the chip head moves to the cold-stored drug solution rack 208 and sucks a buffer (FIG. 13A, Sub-step 15). The reason why a cold-stored drug solution is used is to stop an active biological phenomenon such as a transporter activity, as described above.

The cold-stored drug solution rack 208 is intended for keeping a drug solution, a buffer, or the like at a low temperature for this purpose. The chip head 204 moves to the target well, adds the buffer thereto (FIG. 13A, Sub-step 16), and then moves to the dust box 214 to discard the chip.

The suction head moves to he well filled with the buffer, and removes the buffer (FIG. 13A, Sub-step 17). The removed medium is discarded into the waste liquid tank 206. This step is repeated 3 times in total (washing step) (FIG. 13A, Sub-step 18).

<Sample Preparation: Corresponding to Step 4 in Examples 1 and 2>

After the first temperature-regulating-function-equipped plate holder 210 and the second temperature-regulating-function-equipped plate holder 211 change from 4° C. to 37° C. (FIG. 13A, Sub-step 19), a chip in the chip rack 207 is attached to the chip head 204, the chip head moves to the cold-stored drug solution rack 208, and sucks the buffer (FIG. 13A, Sub-step 20). The chip head 204 moves to the target well, adds the buffer (FIG. 13A, Sub-step 21), and then moves to the dust box 214 to discard the chip.

The device waits at 37° C. for 30 minutes (FIG. 13A, Sub-step 20). Then, the first temperature-regulating-function-equipped plate holder 210 and the second temperature-regulating-function-equipped plate holder 211 change from 37° C. to 4° C. (FIG. 13A, Sub-step 22). Then, a chip in the chip rack 207 is attached to the chip head 204, moves to the well filled with the buffer containing the drug, sucks the drug-containing buffer (supernatant), and dispenses the supernatant to a collection plate for collection on the first plate holder 212 and the second plate holder 213 (collection) (FIG. 13A, Sub-step 23).

<Sample Preparation: Corresponding to 4-Cell Fraction Preparation in Examples 1 and 2>

[For 2D Tissue]

After the first temperature-regulating-function-equipped plate holder 210 and the second temperature-regulating-function-equipped plate holder 211 change from 4° C. to 37° C. (FIG. 14, Sub-step 19), a chip in the chip rack 207 is attached to the chip head 204, and the chip head moves to the normal temperature drug solution rack 209 and sucks 1% TritonX-100 or pure water/methanol (FIG. 14, Sub-step 20).

The chip head 204 moves to a well for Testing section 4 on the first temperature-regulating-function-equipped plate holder (210), adds the 1% TritonX-100 or pure water/methanol (FIG. 14, Sub-step 21), and then moves to the dust box 214 to discard the chip.

A chip in the chip rack 207 is attached to the chip head 204, moves to the well filled with the aforementioned reagent, sucks the whole amount of the cell suspension, and dispenses the cell suspension into the collection plate for collection on the first plate holder 212 (collection) (FIG. 14, Sub-step 22).

In the operation of the device described above, operations in the steps of Testing sections 1 to 3 in Examples 1 and 2 are sequentially performed, but the steps may be performed sequentially or in parallel. In addition, Sub-steps 1 to 18 in FIG. 14 are the same as those in FIG. 13A.

[For 3D Tissue]

After the first temperature-regulating-function-equipped plate holder 210 and the second temperature-regulating-function-equipped plate holder 211 change from 4° C. to 37° C. (FIG. 15A, Sub-step 19), a chip in the chip rack 207 is attached to the chip head 204, and the chip head moves to the normal temperature drug solution rack 209, and sucks trypsin/EDTA (FIG. 15B, Sub-step 20).

The chip head moves to a well for Testing section 4 on the first temperature-regulating-function-equipped plate holder (210), adds the trypsin/EDTA, and then the device waits at 37° C. for 30 minutes (FIG. 15B, Sub-step 21). The chip head sucks 1% TritonX-100 or pure water/methanol (FIG. 15B, Sub-step 22).

The chip head 204 moves to the well for Testing section 4 on the first temperature-regulating-function-equipped plate holder (210), adds the 1% TritonX-100 or pure water/methanol (FIG. 15B, Sub-step 23), and then moves to the dust box 214 to discard the chip.

A chip in the chip rack 207 is attached to the chip head 204, moves to the well filled with the aforementioned reagent, sucks the whole amount of the cell suspension, and dispenses the cell suspension into the collection plate for collection on the first plate holder 212 (collection) (FIG. 15B, Sub-step 24).

In the operation of the device described above, operations in the steps of Testing sections 1 to 3 in Examples 1 and 2 are sequentially performed, but the steps may be performed sequentially or in parallel. In addition, Sub-steps 1 to 18 in FIG. 15A are the same as those in FIG. 13A.

<Sample Preparation: Corresponding to Steps 5 and 6 in Examples 1 and 2>

[For 2D Tissue]

After the first temperature-regulating-function-equipped plate holder 210 changes from 4° C. to 37° C. (FIG. 13A, Sub-step 24), a chip in the chip rack 207 is attached to the chip head 204, the chip head moves to the normal temperature drug solution rack (209), and sucks a buffer containing EGTA (FIG. 13A, Sub-step 25).

The chip head 204 moves to a well for Testing section 1 on the first plate holder 212, adds the buffer containing EGTA (FIG. 13B, Sub-step 26), and then moves to the dust box 214 to discard the chip. The device waits at 37° C. for 30 minutes (FIG. 13B, Sub-step 26).

A chip in the chip rack 207 is attached to the chip head 204, and the chip head moves to the normal temperature drug solution rack 209, and sucks a buffer (FIG. 13B, Sub-step 27).

The chip head 204 moves to a well for Testing section 2 on the first plate holder 212, adds the buffer (FIG. 13B, Sub-step 28), and then moves to the dust box 214 to discard the chip. The device waits at 37° C. for 30 minutes (FIG. 13B, Sub-step 28). A chip in the chip rack 207 is attached to the chip head 204, and the chip head moves to the cold-stored drug solution rack 209, and sucks a buffer (FIG. 13B, Sub-step 29).

The chip head 204 moves to a well for Testing section 3 on the second plate holder 213, adds the buffer (FIG. 13B, Sub-step 30), and then moves to the dust box 214 to discard the chip. The device waits at 4° C. for 30 minutes (FIG. 13B, Sub-step 30). A chip in the chip rack 207 is attached to the chip head 204, moves to the well filled with the EGTA buffer containing the drug, sucks the drug-containing EGTA buffer (supernatant), and dispenses (collects) the supernatant into the collection plate for collection on the first plate holder 212 (FIG. 13B, Sub-step 31).

A chip in the chip rack 207 is attached to the chip head 204, moves to the well filled with the buffer containing the drug, sucks the drug-containing buffer (supernatant), and dispenses (collects) the supernatant into the collection plate for collection on the first plate holder 212 (FIG. 13B, Sub-step 32).

A chip in the chip rack 207 is attached to the chip head 204, moves to the well filled with the EGTA buffer containing the drug, sucks the drug-containing buffer (supernatant), dispenses (collects) the supernatant into the collection plate for collection on the first plate holder 213 (FIG. 13B, Sub-step 33).

After both the first temperature-regulating-function-equipped plate holder 210 and the second temperature-regulating-function-equipped plate holder 211 change to a room temperature (FIG. 13B, Sub-step 34), a chip in the chip rack 207 is attached to the chip head 204, the chip head moves to the normal temperature drug solution rack 209, and sucks 1% TritonX-100 or pure water/methanol (FIG. 13B, Sub-step 35).

The chip head 204 moves to the well for each of Testing sections 1, 2, and 3 on the first temperature-regulating-function-equipped plate holder (210) and the second temperature-regulating-function-equipped plate holder 211, adds the 1% TritonX-100 or pure water/methanol (FIG. 13B, Sub-step 36), and then moves to the dust box 214 to discard the chip.

A chip in the chip rack 207 is attached to the chip head 204, moves to the well filled with the aforementioned reagent, sucks the whole amount of the cell suspension, and dispenses the cell suspension into the collection plate for collection on the first plate holder 212 and the second plate holder 213 (collection) (FIG. 13B, Sub-step 37). In the operation of the device described above, operations in the steps of Testing sections 1 to 3 in Examples 1 and 2 are sequentially performed, but the steps may be performed sequentially or in parallel.

[For 3D Tissue]

After the first temperature-regulating-function-equipped plate holder 210 changes from 4° C. to 37° C. (FIG. 16A, Sub-step 24), a chip in the chip rack 207 is attached to the chip head 204, and the chip head moves to the normal temperature drug solution rack (209), and sucks a buffer containing trypsin/EDTA (FIG. 16B, Sub-step 25).

The chip head 204 moves to a well for Testing section 1 on the first plate holder 212, adds the buffer containing trypsin/EDTA (FIG. 16B, Sub-step 26), and moves to the dust box 214 to discard the chip. The device waits at 37° C. for 30 minutes (FIG. 16B, Sub-step 26). A chip in the chip rack 207 is attached to the chip head 204, and the chip head moves to the normal temperature drug solution rack 209, and sucks a buffer (FIG. 16B, Sub-step 27).

The chip head 204 moves to a well for Testing section 2 on the first plate holder 212, adds the buffer (FIG. 16B, Sub-step 28), and then moves to the dust box 214 to discard the chip. The device waits at 37° C. for 30 minutes (FIG. 16B, Sub-step 28). A chip in the chip rack 207 is attached to the chip head 204, and the chip head moves to the cold-stored drug solution rack 209, and sucks a buffer (FIG. 16B, Sub-step 29).

The chip head 204 moves to a well for Testing section 3 on the second plate holder 213, adds the buffer (FIG. 16B, Sub-step 30), and then moves to the dust box 214 to discard the chip. The device waits at 4° C. for 30 minutes (FIG. 16B, Sub-step 30). A chip in the chip rack 207 is attached to the chip head 204, moves to the well filled with the trypsin/EDTA buffer containing the drug, sucks the cell suspension, and dispenses (collects) the cell suspension into the collection plate for collection on the first plate holder 212 (FIG. 16B, Sub-step 31).

The dispensed plate is subjected to centrifugation in a centrifugation unit to separate into a supernatant and a cell pellet, and then the supernatant is dispensed (collected) into the collection plate for collection on the first plate holder 212 (FIG. 16B, Sub-step 32). Although centrifugation is used here, the method is obviously not limited thereto as long as it can separate the supernatant and the pellet.

A chip in the chip rack 207 is attached to the chip head 204, and the chip head 204 moves to the well filled with the buffer containing the drug, sucks the drug-containing buffer (supernatant), and dispenses (collects) the supernatant into the collection plate for collection on the first plate holder 212 (FIG. 16B, Sub-step 33). A chip in the chip rack 207 is attached to the chip head 204, and the chip head 204 moves to the well filled with the buffer containing the drug, sucks the drug-containing buffer (supernatant), dispenses (collects) the supernatant into the collection plate for collection on the first plate holder 213 (FIG. 16B, Sub-step 34).

After both the first temperature-regulating-function-equipped plate holder 210 and the second temperature-regulating-function-equipped plate holder 211 change to a room temperature (FIG. 16B, Sub-step 35), a chip in the chip rack 207 is attached to the chip head 204, and the chip head 204 moves to the normal temperature drug solution rack 209, and sucks 1% TritonX-100 or pure water/methanol (FIG. 16B, Sub-step 36).

The chip head 204 moves to the well for each of Testing sections 1, 2, and 3 on the first temperature-regulating-function-equipped plate holder (210) and the second temperature-regulating-function-equipped plate holder 211, adds the 1% TritonX-100 or pure water/methanol (FIG. 16B, Sub-step 37), and then moves to the dust box 214 to discard the chip. A chip in the chip rack 207 is attached to the chip head 204, moves to the well filled with the aforementioned reagent, sucks the whole amount of a cell suspension, and dispenses the cell suspension into the collection plate for collection on the first plate holder 212 and the second plate holder 213 (collection) (FIG. 16B, Sub-step 38).

In the operation of the device described above, operations in the steps of Testing sections 1 to 3 in Examples 1 and 2 are sequentially performed, but the steps may be performed sequentially or in parallel. In addition, Sub-steps 1 to 24 in FIG. 16A are the same as those in FIG. 13A.

<Transfer from Sample Preparation Unit to Measurement Unit>

The drug collected on the culture plates is transferred to a measurement unit (FIG. 13B, Sub-step 38). In the measurement unit, the drug is measured by a plate reader or an LCMS (FIG. 13B, Sub-step 39).

<Calculation of Distribution Ratio and Score by Analyzing Unit and Display of Results>

Based on the measurement results, a distribution ratio into fractions and a score are calculated (FIG. 13B, Sub-step 40). Then, the obtained calculation value is shown on the display unit (FIG. 13B, Sub-step 41).

Merely as an example of the configurations explained in Examples 1 to 3 above, the following examples will be mentioned.

<Configuration 1>

It is a component analysis device, comprising a retention unit for retaining a plurality of containers for retaining a liver cell tissue, and an analysis unit for measuring a component supplied to the plurality of containers and analyzing the component thus measured, wherein the plurality of containers are at least a first container and a second container, wherein the first container retains a first solution containing a substance that releases adhesion between multiple cells forming the liver cell tissue, and the second container retains a buffer solution, and wherein the analysis unit measures an amount of the component discharged from the liver cell tissue in the first container into the first solution and an amount of the component discharged from the liver cell tissue in the second container into the buffer liquid in the second container, and analyzes an amount of the component to be discharged via a bile duct in the liver cell tissue.

<Configuration 2>

It is the component analysis device according to Configuration 1, further comprising a temperature regulation unit for regulating a temperature of a liquid in the plurality of containers, wherein the plurality of containers are at least a first container, a second container, and a third container, wherein the third container retains the buffer solution, and wherein the temperature regulation unit makes regulation so that a second temperature inside the third container is lower than a first temperature inside the first container and inside the second container, and wherein the analysis unit measures an amount of the component discharged from the liver cell tissue in the third container to the buffer solution in the third container, and analyzes an amount of the component to be discharged via a transporter of the liver cell tissue and an amount of the component to be discharged from other paths than the transporter and the bile duct in the liver cell tissue.

<Configuration 3>

It is drug component analysis device, comprising a retention unit for retaining a plurality of containers for retaining a liver cell tissue having a drug absorbed therein, a liquid feeding unit for feeding a liquid in the plurality of containers, a temperature regulation unit for regulating a temperature of a liquid in the plurality of containers, and an analysis unit for measuring amounts of the drug in the plurality of containers and analyzing the drug thus measured, wherein the plurality of containers are a first container, a second container, a third container, and a fourth container, wherein the liquid feeding unit feeds a first solution containing a substance that releases adhesion between multiple cells forming the liver cell tissue into the fourth container, feeds the first solution into the first container, and feeds a buffer solution into the second container and the third container, wherein the temperature regulation unit regulates a temperature so that a temperature inside the third container is lower than a temperature inside the first container and inside the second container, and wherein the analysis unit analyzes an amount of the drug discharged from the liver cell tissue in the first container to the first solution, an amount of the drug discharged from the liver cell tissue in the second container to the buffer solution in the second container, an amount of the drug discharged from the liver cell tissue in the third container to the buffer solution in the third container, an amount of the drug discharged from the liver cell tissue in the fourth container to the buffer solution in the fourth container, an amount of the drug to be discharged from a transporter in the liver cell tissue, an amount of the drug to be discharged from a bile duct in the liver cell tissue, and an amount of the component to be discharged from other paths than the transporter and the bile duct in the liver cell tissue.

<Configuration 4>

It is a component analysis method, including an analyzing step for measuring a component fed into a plurality of containers retaining a liver cell tissue and analyzing the component thus measured, wherein the plurality of containers are at least a first container and a second container, wherein the first container retains a first solution containing a substance that releases adhesion between multiple of cells forming the liver cell tissue, and wherein the second container retains a buffer solution, and wherein in the analyzing step, an amount of the component discharged from the liver cell tissue in the first container into the first solution and an amount of the component discharged from the liver cell tissue in the second container into the buffer solution in the second container are measured and an amount of the component to be discharged via a bile duct in the liver cell tissue is analyzed.

<Configuration 5>

It is the component analysis method according to the configuration 4, further comprising a temperature regulating step for regulating a temperature of a liquid in the plurality of containers, wherein the plurality of containers are at least the first container, the second container, and a third container, wherein the third container retains the buffer solution, and wherein in the temperature regulating step, a second temperature inside the third container is regulated to be lower than a first temperature inside the first container and inside the second container, and wherein in the analyzing step, an amount of the component discharged from the liver cell tissue in the third container into the buffer solution in the third container is measured, and an amount of the component to be discharged via a transporter in the liver cell tissue and an amount of the component to be discharged from other paths than the transporter and the bile duct in the liver cell tissue are analyzed.

<Configuration 6>

It is a drug component analysis method, comprising a liquid feeding step for feeding a liquid in a plurality of containers retaining a liver cell tissue having a drug absorbed therein, a temperature regulating step for regulating a temperature of a liquid in the plurality of container, and an analyzing step for measuring amounts of the drug in the plurality of containers and analyzing the drug thus measured, wherein the plurality of containers are a first container, a second container, a third container, and a fourth container, wherein in the liquid feeding step, a first solution containing a substance that releases adhesion between multiple cells forming the liver cell tissue is fed to the fourth container, the first solution is fed to the first container, and a buffer solution is fed to the second container and the third container, wherein in the temperature regulating step, a temperature is regulated so that the temperature inside the third container becomes lower than a temperature inside the first container and inside the second container, and wherein in the analyzing step, an amount of the drug discharged from the liver cell tissue in the first container into the first solution, an amount of the drug discharged from the liver cell tissue in the second container into the buffer solution in the second container, an amount of the drug discharged from the liver cell tissue in the third container into the buffer solution in the third container, an amount of the drug discharged from the liver cell tissue in the fourth container into the buffer solution in the fourth container, an amount of the drug to be discharged from a transporter in the liver cell tissue, an amount of the drug to be discharged from a bile duct in the liver cell tissue, and an amount of the component to be discharged from other paths than the transporter and the bile duct in the liver cell tissue are analyzed.

REFERENCE SIGNS LIST 001 culture plate
002 well
106 culturing unit
107 sample preparation unit
107A input unit
107B temperature regulation unit
107C liquid feeding unit
107D centrifugation unit
108 analysis unit
108A measurement unit
108B analyzing unit
109 display unit
201 syringe pump controller
202 temperature regulation controller
203 syringe pump
204 chip head
205 suction head
206 waste liquid tank
207 chip rack
208 cold-stored drug solution rack
209 normal temperature drug solution rack
210 first temperature-regulating-function-equipped plate holder
211 second temperature-regulating-function-equipped plate holder
212 first plate holder
213 second plate holder
214 dust box
215 circulator
216 suction pump
301 sucked liquid
302 chip

The invention claimed is:

1. A component analysis method, comprising:
providing a plurality of containers including a first container and a second container, wherein the first container comprises contents of liver cell tissue comprising a 3D culture and a first solution containing a first substance that releases adhesion between multiple cells that form the liver cell tissue and that allows a bile duct formed in the liver cell tissue to collapse, and a substance that comprises trypsin and EDTA for cutting the 3D culture liver cell tissue into single sells, wherein a temperature in the first container is maintained at 37° C., such that a fraction discharged from cells into a blood vessel side includes a fraction via passive diffusion and a fraction via a transporter, and
the second container comprises contents of liver cell tissue comprising a 3D culture and a buffer solution;
contacting the contents of the first container and the contents of the second container with a component;
measuring an amount of the component discharged from the liver cell tissue in the first container into the first solution;
measuring an amount of the component discharged from the liver cell tissue in the second container into the buffer solution in the second container; and
measuring an amount of the component to be discharged via a bile duct in the liver cell tissue.

2. The component analysis method according to claim 1, further comprising:
regulating a temperature of a liquid in a third container and in the first container and the second container, such that a second temperature inside the third container is lower than a first temperature inside the first container and inside the second container, wherein the third container contains the buffer solution; and
measuring an amount of the component discharged from the liver cell tissue in the third container into the buffer solution in the third container;
measuring an amount of the component to be discharged via a transporter in the liver cell tissue; and
measuring an amount of the component to be discharged from paths other than the transporter and the bile duct in the liver cell tissue.

3. A drug component analysis method, comprising
feeding a liquid into a plurality of containers each containing liver cell tissue comprising a 3D culture having a drug absorbed therein,
regulating a temperature of respective liquids in the plurality of containers, and
measuring an amount of the drug in the plurality of containers and analyzing the drug thus measured, wherein the plurality of containers include a first container, a second container, a third container, and a fourth container,
wherein in the liquid feeding step, a first solution containing a substance that releases adhesion between multiple cells forming the liver cell tissue and that allows a bile duct formed in the liver cell tissue to collapse, and a substance that comprises trypsin and EDTA for cutting the 3D culture liver cell tissue into single sells is fed in the first container, wherein a temperature in the first container is maintained at 37° C., such that a fraction discharged from cells into a blood vessel side includes a fraction via passive diffusion and a fraction via a transporter, and a buffer solution is fed to the second container and the third container, wherein in the temperature regulating step, the temperatures of the plurality of containers are regulated so that a temperature inside the third container is lower than a temperature inside the first container and inside the second container, and wherein the method further comprises:

measuring an amount of the drug discharged from the liver cell tissue in the first container into the first solution, measuring an amount of the drug discharged from the liver cell tissue in the second container into the buffer solution in the second container, measuring an amount of the drug discharged from the liver cell tissue in the third container into the buffer solution in the third container, measuring an amount of the drug discharged from the liver cell tissue in the fourth container into the buffer solution in the fourth container, measuring an amount of the drug to be discharged from a transporter in the liver cell tissue, measuring an amount of the drug to be discharged from a bile duct in the liver cell tissue, and measuring an amount of the drug to be discharged from paths other than the transporter and the bile duct in the liver cell tissue.

4. The component analysis method according to claim 1, further comprising the step of determining a distribution ratio into fractions of the component based on at least one of the measured amount of the component discharged from the liver cell tissue in the first container into the first solution and the measured amount of the component discharged from the liver cell tissue in the second container into the buffer solution in the second container.

5. The drug component analysis method according to claim 3, further comprising the step of determining a distribution ratio into fractions of the component based on at least one of the measured amount of the drug discharged from the liver cell tissue in the first container into the first solution and the measured amount of the drug discharged from the liver cell tissue in the second container into the buffer solution in the second container.

* * * * *